United States Patent
Al-Jumaily et al.

(10) Patent No.: US 11,109,791 B2
(45) Date of Patent: Sep. 7, 2021

(54) DIAGNOSIS AND MONITORING OF CARDIO-RESPIRATORY DISORDERS

(71) Applicants: ResMed Pty Ltd, Bella Vista (AU); University of Technology Sydney, Ultimo (AU)

(72) Inventors: Adel Ali Al-Jumaily, Sydney (AU); Vinh Phuc Tran, Sydney (AU)

(73) Assignee: ResMed Pty Ltd

( * ) Notice: Subject to any disclaimer, the term of this patent is extended or adjusted under 35 U.S.C. 154(b) by 418 days.

(21) Appl. No.: 15/579,839

(22) PCT Filed: Jun. 24, 2016

(86) PCT No.: PCT/AU2016/050542
§ 371 (c)(1),
(2) Date: Dec. 5, 2017

(87) PCT Pub. No.: WO2016/205891
PCT Pub. Date: Dec. 29, 2016

(65) Prior Publication Data
US 2018/0153427 A1    Jun. 7, 2018

(30) Foreign Application Priority Data

Jun. 26, 2015 (AU) .............................. 2015902494
Mar. 10, 2016 (AU) .............................. 2016900897

(51) Int. Cl.
*A61B 5/04*   (2006.01)
*A61B 5/316*  (2021.01)
(Continued)

(52) U.S. Cl.
CPC .............. *A61B 5/316* (2021.01); *A61B 5/021* (2013.01); *A61B 5/024* (2013.01); *A61B 5/0205* (2013.01);
(Continued)

(58) Field of Classification Search
CPC ........... A61B 5/0205; A61B 5/00; A61B 5/08; A61B 5/087; A61M 16/00
(Continued)

(56) References Cited

U.S. PATENT DOCUMENTS

| 4,944,310 A | 7/1990 | Sullivan |
| 6,532,959 B1 | 3/2003 | Berthon-Jones |

(Continued)

FOREIGN PATENT DOCUMENTS

| WO | 2010091168 A1 | 8/2010 |
| WO | 2013037399 A1 | 3/2013 |

OTHER PUBLICATIONS

International Search Report to PCT Application No. PCT/AU2016/050542.
(Continued)

*Primary Examiner* — Jon Eric C Morales
(74) *Attorney, Agent, or Firm* — Botos Churchill IP Law LLP

(57) ABSTRACT

Methods and systems estimate cardio-respiratory parameter(s), such as from in-phase and quadrature channels. The channels may represent patient chest movement and may be generated with a sensor, such as a contactless sensor that may sense movement with radio-frequency signals. In the methods/systems, the in-phase and quadrature channels may be processed, such as in a processor(s), using relative demodulation to generate cardio-respiratory parameter estimate(s). Optionally, the processing produces a jerk signal that may be filtered for producing a heart rate estimate, such as from zero-crossings of the filtered signal. Optionally, the processing produces a chest velocity signal that may be filtered for producing a respiratory rate estimate, such as from zero-crossings of the filtered signal. Optionally, a respiratory volume, such as tidal volume, may be esti-
(Continued)

mated from an intrapulmonary pressure signal generated by applying a function to a chest displacement signal where the function relates intrapulmonary pressure and chest displacement.

43 Claims, 16 Drawing Sheets

(51) Int. Cl.
*A61B 5/0205* (2006.01)
*A61B 5/113* (2006.01)
*A61B 5/024* (2006.01)
*A61B 5/0507* (2021.01)
*A61B 5/021* (2006.01)
*A61B 5/00* (2006.01)
*A61B 5/087* (2006.01)
*A61B 5/097* (2006.01)
*A61B 5/026* (2006.01)
*A61B 5/08* (2006.01)

(52) U.S. Cl.
CPC ............ *A61B 5/0507* (2013.01); *A61B 5/113* (2013.01); *A61B 5/6803* (2013.01); *A61B 5/0006* (2013.01); *A61B 5/0261* (2013.01); *A61B 5/087* (2013.01); *A61B 5/0816* (2013.01); *A61B 5/0873* (2013.01); *A61B 5/097* (2013.01)

(58) Field of Classification Search
USPC ........................................................ 600/301
See application file for complete search history.

(56) References Cited

U.S. PATENT DOCUMENTS

| | | |
|---|---|---|
| 8,968,203 B2 | 3/2015 | Palti |
| 2009/0278728 A1 | 11/2009 | Morgan et al. |
| 2010/0204550 A1* | 8/2010 | Heneghan ............ A61B 5/4818 |
| | | 600/301 |
| 2017/0238867 A1* | 8/2017 | Javed .................... A61B 5/486 |

OTHER PUBLICATIONS

Wade, O., "Movements of the thoracic cage and diaphragm in respiration", The Journal of Physiology 124.2 (1954): 193-212.

Pan, J. and Tompkins, W. J., A Real-Time QRS Detection Algorithm. IEEE Transactions on Biomedical Engineering, 1985. BME-32(3), p. 230-236.

W. R. Stahl, Scaling of respiratory variables in mammals, Journal of Applied Physiology, vol. 22, No. 3, 1967, pp. 453-460.

E. H. Livingston, and S. Lee, Body surface area prediction in normal-weight and obese patients, American Journal of Physiology—Endocrinology and Metabolism, vol. 281, No. 3, 2001., pp. E586-E591.

* cited by examiner

DIAGNOSIS AND MONITORING OF CARDIO-RESPIRATORY DISORDERS

1 CROSS-REFERENCE TO RELATED APPLICATIONS

The present application is a national phase entry under 35 U.S.C. § 371 of International Application No. PCT/AU2016/050542 filed Jun. 24, 2016, published in English, which claims priority from Australian Patent Application Nos. 2016900897 filed Mar. 10, 2016 and 2015902494 filed Jun. 26, 2015, all of which are incorporated herein by reference.

2 STATEMENT REGARDING FEDERALLY SPONSORED RESEARCH OR DEVELOPMENT

Not Applicable

3 SEQUENCE LISTING

Not Applicable

4 BACKGROUND OF THE TECHNOLOGY

4.1 Field of the Technology

The present technology relates to one or more of the detection, diagnosis, monitoring, treatment, prevention and amelioration of cardio-respiratory disorders. The present technology also relates to medical devices or apparatus, and their use.

4.2 Description of the Related Art 4.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inspired air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for cardio-respiratory disorders in which the lungs are unable to inspire sufficient oxygen or expire sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Heart failure (HF) is a relatively common and severe cardio-respiratory disorder, characterised by the inability of the heart to keep up with the oxygen demands of the body. Management of heart failure is a significant challenge to modern healthcare systems due to its high prevalence and severity. HF is a chronic condition, which is progressive in nature. The progression of HF is often characterized as relatively stable over long periods of time (albeit with reduced cardiovascular function) punctuated by episodes of an acute nature. In these acute episodes, the patient experiences worsening of symptoms such as dyspnea (difficulty breathing), gallop rhythms, increased jugular venous pressure, and orthopnea. This is typically accompanied by overt congestion (which is the buildup of fluid in the pulmonary cavity). This excess fluid often leads to measurable weight gain of several kilograms. In many cases, however, by the time overt congestion has occurred, there are limited options for the doctor to help restabilise the patients, and in many cases the patient requires hospitalization. In extreme cases, without timely treatment, the patient may undergo acute decompensated heart failure (ADHF) events, sometimes referred to as decompensations.

4.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

4.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

4.2.4 Diagnosis and Monitoring Systems

Diagnosis is the identification of a condition from its signs and symptoms. Diagnosis tends to be a one-off process, whereas monitoring the progress of a condition can continue indefinitely. Some diagnosis systems are suitable only for diagnosis, whereas some may also be used for monitoring.

It is of interest to be able to monitor HF or COPD patients at home with a view to preventing or ameliorating potential clinical events such as HF decompensations or COPD exacerbations. Characteristics that have been proposed or used for the purpose of predicting clinical events include body weight, levels of B natriuretic peptides (BNP), nocturnal heart rate, and changes in sleeping posture. Polysomnography (PSG) is a conventional system for diagnosis and monitoring of cardio-respiratory disorders, and typically involves expert clinical staff to apply the system. PSG typically involves the placement of 15 to 20 contact sensors on a patient in order to record various biosignals such as electroencephalography (EEG), electrocardiography (ECG), electrooculograpy (EOG), electromyography (EMG), etc. PSG is therefore expensive and inconvenient. In particular it is unsuitable for home diagnosis and monitoring.

COPD and HF diagnosis/monitoring systems based on the sensor modalities described above tend to be unsatisfactory as they require good patient compliance (e.g. weight-based monitoring systems that rely on patients to record their daily weights), are wearable, which makes them unrealistic for long-term monitoring, or are invasive or obtrusive. The use of implantable devices is only feasible for a subset of HF patients eligible for such devices.

SleepMinder (ResMed Sensor Technologies Ltd, Dublin, Ireland) is a contactless bedside monitor suitable for long-term monitoring of chronic diseases such as HF and COPD. SleepMinder contains a biomotion transceiver sensor operating on radar principles in a license-free band at 5.8 GHz or 10.5 GHz at ultra-low power (less than 1 mW). SleepMinder is capable of measuring bodily movement, and in particular cardio-respiratory movement, over a distance ranging from 0.3 to 1.5 metres; in the case of two people in a bed, a combination of sophisticated sensor design and intelligent signal processing allows SleepMinder to measure only the movement of the person nearest to the sensor. The SleepMinder is suitable for long-term monitoring of chronic disease as it is unobtrusive and does not present significant compliance issues. However, processing the raw SleepMinder signals to obtain cardio-respiratory parameters useful for chronic HF or COPD monitoring, such as heart rate and respiratory rate, is a difficult task.

5 BRIEF SUMMARY OF THE TECHNOLOGY

The present technology is directed towards providing medical devices used in the diagnosis, monitoring, amelioration, treatment, or prevention of cardio-respiratory disorders having one or more of improved comfort, cost, efficacy, ease of use and manufacturability.

A first aspect of the present technology relates to apparatus used in the diagnosis or monitoring of a cardio-respiratory disorder.

Another aspect of the present technology relates to methods used in the diagnosis or monitoring of a cardio-respiratory disorder.

One form of the present technology comprises a monitoring apparatus including a contactless motion sensor, and a processor configured to analyse in-phase and quadrature channels (i.e., the I and Q channels respectively) from the sensor to estimate a patient's cardio-respiratory parameters such as heart rate, respiratory rate, and/or tidal volume. Rather than demodulating the I and Q channels into a general motion signal and analysing the general motion signal to separate specific cardiac and respiratory components, the analysis obtains a cardiac "jerk" and/or a respiratory velocity directly from the I and Q channels. The zero-crossings of these signals may be determined and may be used to obtain estimates of heart rate and respiratory rate respectively. The chest velocity may be integrated to obtain chest displacement of the patient, to which a pulmonary ventilation model may be applied to estimate instantaneous intrapulmonary pressure, from which an estimate of mean tidal volume may in turn be derived.

Some versions of the present technology include a method of estimating a heart rate of a patient from an in-phase channel and a quadrature channel. Each channel may represent chest movement of the patient. The method may operate in one or more processors. The method may include processing the in-phase channel and the quadrature channel by relative demodulation to generate a jerk signal. The method may include filtering the jerk signal with a cardiac band-pass filter to produce a cardiac jerk signal. The method may include generating a heart rate estimate from zero-crossings of the cardiac jerk signal.

In some versions, the generating the heart rate estimate may include detecting systole phases of heartbeats by determination of the zero-crossings of the cardiac jerk signal; and calculating the heart rate estimate from a number of detected systole phases in a window of the cardiac jerk signal. The generating the heart rate estimate may include detecting diastole phases of heartbeats by determination of the zero-crossings of the cardiac jerk signal; and calculating the heart rate estimate from a number of detected diastole phases in a window of the cardiac jerk signal. The jerk signal may be a third derivative of chest displacement of the patient.

In some versions, the relative demodulation may involve numerically differentiating the in-phase channel and the quadrature channel to produce a numeric derivative of the in-phase channel and a numeric derivative of the quadrature channel. The relative demodulation may involve generating a chest velocity signal from the numeric derivative of the in-phase channel and the numeric derivative of the quadrature channel. The relative demodulation may involve numerically differentiating the chest velocity signal to generate the jerk signal.

In some cases, the generating the chest velocity signal may include dividing the numeric derivative of the quadrature channel by the in-phase channel to obtain a first ratio signal; dividing the numeric derivative of the in-phase channel by the quadrature channel to obtain a second ratio signal; and subtracting the second ratio signal from the first ratio signal multiplied by a scaling factor. The scaling factor may be a ratio of amplitude gain constants of the in-phase channel and the quadrature channel. The method may include subtracting respective offsets from the in-phase channel and the quadrature channel before the dividing steps.

Optionally, the cardiac band-pass filter may comprise a band-pass filter with a pass-band of 0.7 to 1.6 Hz. The band-pass filter may be a sixth-order Butterworth filter. The in-phase channel and the quadrature channel may be generated by a contactless motion sensor. The contactless motion sensor may be a radio-frequency sensor that generates the in-phase channel and the quadrature channel by processing of signals representing transmitted radio-frequency waves and received reflected ones of the transmitted radio-frequency waves. The one or more processors may control a display to output the heart rate estimate. The one or more processors may control a change to a control parameter of a treatment device in response to the heart rate estimate.

Some versions of the present technology include an apparatus or systems configured with any of such methods of estimating a heart rate.

For example, some versions of the present technology include apparatus for estimating heart rate of a patient. The apparatus may include a contactless motion sensor configured to generate an in-phase channel and a quadrature channel. The in-phase channel and the quadrature channel may each represent chest movement of the patient when the contactless motion sensor is generally directed toward a chest of the patient. The apparatus may include a processor configured to analyse the in-phase channel and the quadrature channel to generate a heart rate estimate. The analysis may include processing the in-phase channel and the quadrature channel by relative demodulation to generate a jerk signal. The analysis may include filtering the jerk signal with a cardiac band-pass filter to produce a cardiac jerk signal. The analysis may include generating a heart rate estimate from zero-crossings of the cardiac jerk signal.

The processor may be co-located with the contactless motion sensor. The apparatus may include communications circuitry configured to transfer data to an external computing device via a connection. The processor may be a processor of the external computing device. The contactless motion sensor may be a radio-frequency sensor that generates the in-phase channel and the quadrature channel by processing of signals representing transmitted radio-frequency waves and received reflected ones of the transmitted radio-frequency waves.

Some versions of the present technology include a patient monitoring system. The system may include means for generating an in-phase channel and a quadrature channel, each channel representing chest movement of a patient. The system may include means for analysing the in-phase channel and the quadrature channel to generate a heart rate estimate of the patient. The analysing of this means may include processing the in-phase channel and the quadrature channel by relative demodulation to generate a jerk signal; The analysing of this means may include filtering the jerk signal with a cardiac band-pass filter to produce a cardiac jerk signal. The analysing of this means may include generating a heart rate estimate from zero-crossings of the cardiac jerk signal.

Some versions of the present technology include a method of estimating a respiratory rate of a patient from an in-phase channel and a quadrature channel. Each channel may represent chest movement of the patient. The method may operate in one or more processors. The method may include processing the in-phase channel and the quadrature channel by relative demodulation to generate a chest velocity signal. The method may include filtering the chest velocity signal with a respiratory band-pass filter to produce a respiratory velocity signal. The method may include generating a respiratory rate estimate from zero-crossings of the respiratory velocity signal.

In some versions, the generating the respiratory rate estimate may include detecting inspiration phases of respiration by determination of the zero-crossings of the respiratory velocity signal. The generating the respiratory rate estimate may include calculating the respiratory rate estimate from a number of detected inspiration phases in a window of the respiratory velocity signal.

In some versions, the generating the respiratory rate estimate may include detecting expiration phases of respiration by determination of the zero-crossings of the respiratory velocity signal. The generating the respiratory rate estimate may include calculating the respiratory rate estimate from a number of detected expiration phases in a window of the respiratory velocity signal. The chest velocity signal may be a first derivative of chest displacement of the patient.

In some versions, the relative demodulation may involve numerically differentiating the in-phase channel and the quadrature channel to produce a numeric derivative of the in-phase channel and a numeric derivative of the quadrature channel. The relative demodulation may involve generating a chest velocity signal from the numeric derivative of the in-phase channel and the numeric derivative of the quadrature channel.

In some versions, the generating the chest velocity signal may include dividing the numeric derivative of the quadrature channel by the in-phase channel to obtain a first ratio signal; dividing the numeric derivative of the in-phase channel by the quadrature channel to obtain a second ratio signal; and subtracting the second ratio signal from the first ratio signal multiplied by a scaling factor. The scaling factor may be a ratio of amplitude gain constants of the in-phase channel and the quadrature channel. The method may also include subtracting respective offsets from the in-phase channel and the quadrature channel before the dividing steps. Optionally, the respiratory band-pass filter may include a band-pass filter with a pass-band of 0.2 to 0.5 Hz. The band-pass filter may be a sixth-order Butterworth filter.

The in-phase channel and the quadrature channel may be generated by a contactless motion sensor. The contactless motion sensor may be a radio-frequency sensor that generates the in-phase channel and quadrature channel by processing of signals representing transmitted radio-frequency waves and received reflected ones of the transmitted radio-frequency waves. The one or more processors may control a display to output the respiratory rate estimate. The one or more processors may control a change to a control parameter of a treatment device in response to the respiratory rate estimate.

Some versions of the present technology include an apparatus or systems configured with any of such methods of estimating a respiratory rate.

For example, some versions of the present technology include apparatus for estimating respiratory rate of a patient. The apparatus may include a contactless motion sensor configured to generate an in-phase channel and a quadrature channel, each channel representing chest movement of the patient when the contactless motion sensor is generally directed toward a chest of the patient. The apparatus may include a processor configured to analyse the in-phase channel and the quadrature channel to generate a respiratory rate estimate. This analysis may include processing the in-phase channel and the quadrature channel by relative demodulation to generate a chest velocity signal. This analysis may include filtering the chest velocity signal with a respiratory band-pass filter to produce a respiratory velocity signal. This analysis may include generating a respiratory rate estimate from zero-crossings of the respiratory velocity signal. The processor may be co-located with the contactless motion sensor. The apparatus may further comprising communications circuitry configured to transfer data to an external computing device via a connection. The processor may be a processor of the external computing device. The contactless motion sensor may be a radio-frequency sensor that generates the in-phase channel and the quadrature channel by processing of signals representing transmitted radio-frequency waves and received reflected ones of the transmitted radio-frequency waves.

Some versions of the present technology include a patient monitoring system. The system may include means for generating an in-phase channel and a quadrature channel, each channel representing chest movement of a patient. The system may include means for analysing the in-phase channel and the quadrature channel to generate a respiratory rate estimate of the patient. This analysing may include processing the in-phase channel and the quadrature channel by relative demodulation to generate a chest velocity signal. This analysing may include filtering the chest velocity signal with a respiratory band-pass filter to produce a respiratory velocity signal. This analysing may include generating a respiratory rate estimate from zero-crossings of the respiratory velocity signal.

Some versions of the present technology include a method of estimating a tidal volume of a patient. The method may operate in one or more processors. The method may include generating an intrapulmonary pressure signal by applying a function relating intrapulmonary pressure and chest displacement to a signal representing chest displacement of the patient. The method may include generating a tidal volume estimate from the intrapulmonary pressure signal.

In some versions, the method may include processing, by relative demodulation, an in-phase channel and a quadrature channel, each channel representing chest movement of the patient, to generate a chest velocity signal. The method may include numerically integrating the chest velocity signal to obtain the chest displacement signal.

The function relating intrapulmonary pressure and chest displacement may include input for a respiratory rate of the patient. The method may include generating, for the function, a respiratory rate estimate of the patient from the chest velocity signal. The generating the respiratory rate estimate may include processing the in-phase channel and the quadrature channel by relative demodulation to generate a chest velocity signal; filtering the chest velocity signal with a respiratory band-pass filter to produce a respiratory velocity signal; and generating a respiratory rate estimate from zero-crossings of the respiratory velocity signal. The relative demodulation may include numerically differentiating the in-phase channel and the quadrature channel to produce a numeric derivative of the in-phase channel and a numeric derivative of the quadrature channel; and generating a chest velocity signal from the numeric derivative of the in-phase channel and the numeric derivative of the quadrature channel.

In some cases, the generating the tidal volume estimate may include estimating an instantaneous lung volume from the intrapulmonary pressure signal; applying a respiratory band-pass filter to the instantaneous lung volume to extract a respiratory component of the instantaneous lung volume; and generating the tidal volume estimate for a breath by determining a difference between maxima and minima of the respiratory component of the instantaneous lung volume over the breath. The method may also include calculating a mean of the tidal volume estimate for each breath in a window. The function relating intrapulmonary pressure and chest displacement may include input for a body mass index of the patient. The one or more processors may control a display to output the tidal volume estimate. The one or more processors may control a change to a control parameter of a treatment device in response to the tidal volume estimate.

Some versions of the present technology include an apparatus or systems configured with any of such methods of estimating a tidal volume.

For example, some versions of the technology may include apparatus for estimating a tidal volume of a patient. The apparatus may include a sensor configured to generate a signal representing chest displacement of the patient. The apparatus may include a processor configured to analyse the chest displacement signal to generate a tidal volume estimate. The analysis may involve generating an intrapulmonary pressure signal by applying a function relating intrapulmonary pressure and chest displacement to a signal representing chest displacement of the patient; and generating a tidal volume estimate from the intrapulmonary pressure signal. The sensor may be a contactless motion sensor configured to generate an in-phase channel and a quadrature channel. Each channel may represent chest movement of the patient when the contactless motion sensor is generally directed toward a chest of the patient. The processor may be further configured to process the in-phase channel and the quadrature channel by relative demodulation to generate a chest velocity signal. The processor may be further configured to numerically integrate the chest velocity signal to obtain the chest displacement signal. The contactless motion sensor may be a radio-frequency sensor that generates the in-phase channel and the quadrature channel by processing of signals representing transmitted radio-frequency waves and received reflected ones of the transmitted radio-frequency waves. The processor may be co-located with the sensor. The apparatus may include communications circuitry configured to transfer data to an external computing device via a connection. The processor may be a processor of the external computing device.

Some versions of the present technology include a patient monitoring system. The system may include means for generating a signal representing chest displacement of a patient. The system may include means for analysing the chest displacement signal to generate a tidal volume estimate of the patient. The means for analysing may include generating an intrapulmonary pressure signal by applying a function relating intrapulmonary pressure and chest displacement to a signal representing chest displacement of the patient. The means for analysing may include generating a tidal volume estimate from the intrapulmonary pressure signal.

Some versions of the present technology include a method of estimating a cardio-respiratory parameter of a patient from an in-phase channel and a quadrature channel. Each channel may represent chest movement of the patient. The method may operate in one or more processors. The method may include receiving the in-phase channel and the quadrature channel. The method may include processing the in-phase channel and the quadrature channel by relative demodulation to generate a chest velocity signal. The method may include generating a cardio-respiratory parameter estimate based on the chest velocity signal.

In some versions, the relative demodulation comprises: numerically differentiating the in-phase channel and the quadrature channel to produce a numeric derivative of the in-phase channel and a numeric derivative of the quadrature channel; and generating the chest velocity signal from the numeric derivative of the in-phase channel and the numeric derivative of the quadrature channel.

Optionally, the cardio-respiratory parameter may be respiratory rate, and the generating may include: filtering the chest velocity signal with a respiratory band-pass filter to produce a respiratory velocity signal; and generating a respiratory rate estimate from zero-crossings of the respiratory velocity signal.

The relative demodulation may further include numerically differentiating the chest velocity signal to generate a jerk signal. Optionally, the cardio-respiratory parameter may be heart rate, and the generating may include filtering the jerk signal with a cardiac band-pass filter to produce a cardiac jerk signal; and generating a heart rate estimate from zero-crossings of the cardiac jerk signal.

Optionally, the cardio-respiratory parameter may be tidal volume, and the generating may involve: numerically integrating the chest velocity signal to obtain a chest displacement signal, generating an intrapulmonary pressure signal by applying a function relating intrapulmonary pressure and chest displacement to the chest displacement signal; and generating a tidal volume estimate from the intrapulmonary pressure signal.

Some versions of the present technology include an apparatus or systems configured with any of such methods of estimating a cardio-respiratory parameter.

For example, some versions of the present technology include apparatus for estimating a cardio-respiratory parameter of a patient. The apparatus may include a contactless motion sensor configured to generate an in-phase channel and a quadrature channel, wherein the in-phase channel and the quadrature channel may each represent chest movement of the patient when the contactless motion sensor is generally directed toward a chest of the patient. The apparatus may include a processor configured to analyse the in-phase channel and the quadrature channel to generate a cardio-respiratory parameter estimate. This analysis may involve reception of the in-phase channel and the quadrature channel; processing the in-phase channel and the quadrature channel by relative demodulation to generate a chest velocity signal; and generation of a cardio-respiratory parameter estimate based on the chest velocity signal.

Some versions of the present technology include a patient monitoring system. The system may include means for generating an in-phase channel and a quadrature channel, each channel representing chest movement of a patient. The system may include means for analysing the in-phase channel and the quadrature channel to generate a cardio-pulmonary parameter estimate of the patient. This analysing may involve receiving the in-phase channel and the quadrature channel; processing the in-phase channel and the quadrature channel by relative demodulation to generate a chest velocity signal; and generating a cardio-respiratory parameter estimate based on the chest velocity signal.

Any of the estimates herein may be generated, such as by a processor, as or for output. For example, they may be generated for display on a display device that is controlled by a processor. Once generated they may be evaluated for generating some other output on the display device where the displayed output is based on the evaluation of the estimate(s). Any one or more of the estimates may be applied as an input to a control algorithm for a treatment device, such as a respiratory pressure therapy device described herein or other cardiac-related treatment device (e.g., a cardiac resynchronization device, cardioverter-defibrillator, etc.). Thus, an output of the treatment device may be generated based on the one or more estimates. For example, any one of more of the estimates may serve as an input to control a change to a control parameter (e.g., a generated pressure treatment or cardiac stimulation treatment) of such a treatment device.

The methods, systems, devices and apparatus described herein can provide improved functioning in a processor, such as of a processor of a specific purpose computer, and/or a cardio-respiratory diagnosis/monitoring apparatus. Moreover, in some cases they may be integrated within a controller or processor of a treatment device such as a respiratory pressure therapy device or a cardiac-related treatment device. Moreover, the described methods, systems, devices and apparatus can provide improvements in the technological field of automated management, monitoring and/or treatment of cardiac conditions and/or respiratory conditions, including, for example, sleep disordered breathing or respiratory insufficiency (e.g., COPD).

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

6 BRIEF DESCRIPTION OF THE DRAWINGS

The present technology is illustrated by way of example, and not by way of limitation, in the figures of the accompanying drawings, in which like reference numerals refer to similar elements including:

6.1 Treatment Systems

FIG. 1 shows a system including a patient 1000 wearing a patient interface 3000, in the form of a full-face mask, receiving a supply of air at positive pressure from an RPT device 4000. Air from the RPT device 4000 is humidified in a humidifier 5000, and passes along an air circuit 4170 to the patient 1000.

6.2 Respiratory System and Facial Anatomy

FIG. 2 shows an overview of a human respiratory system including the nasal and oral cavities, the larynx, vocal folds, oesophagus, trachea, bronchus, lung, alveolar sacs, heart and diaphragm.

6.3 Patient Interface

FIG. 3 shows a patient interface in the form of a nasal mask in accordance with one form of the present technology.

6.4 RPT Device

6.5 Humidifier

Figure 1:
Figure 2:
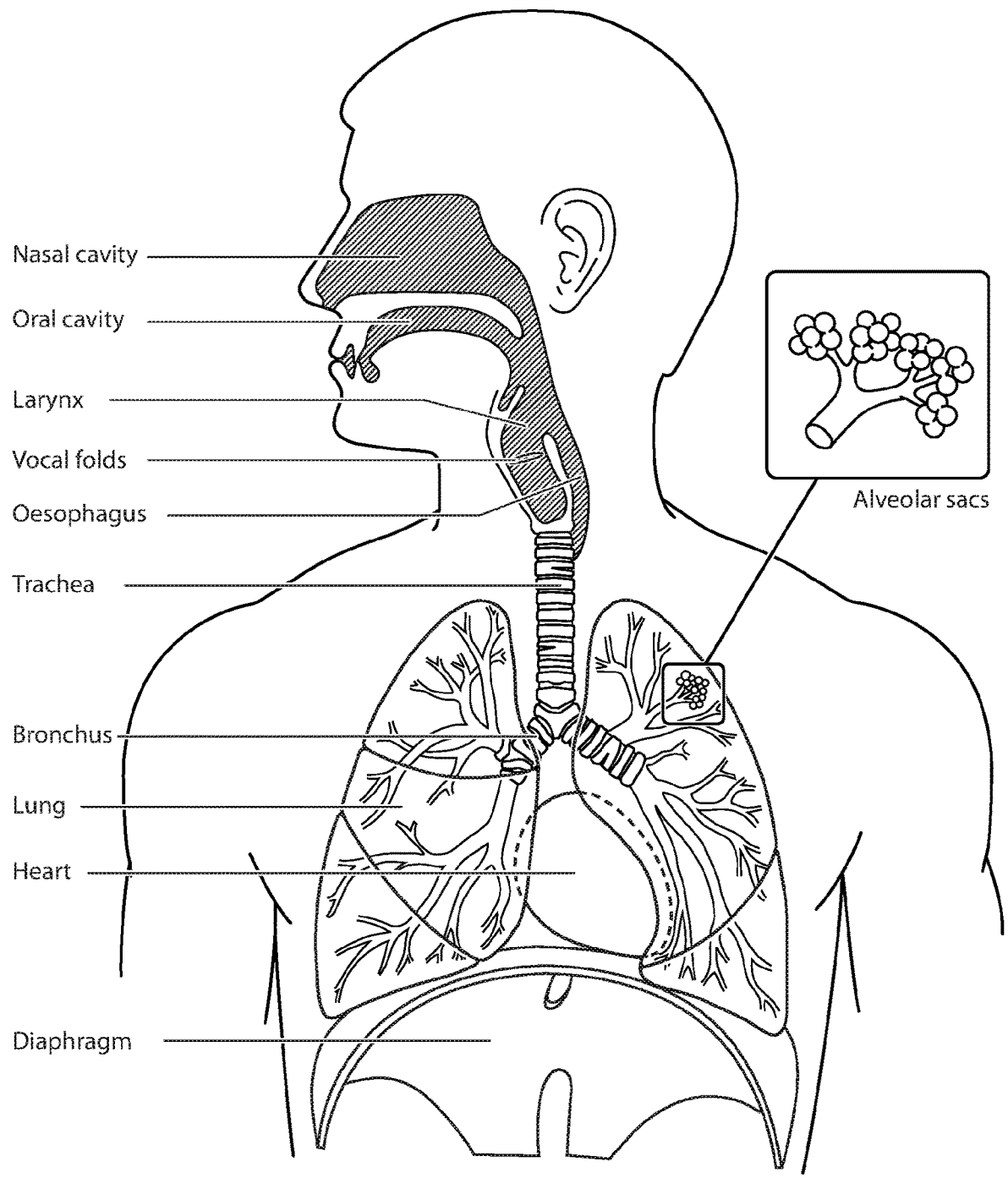
Figure 3:
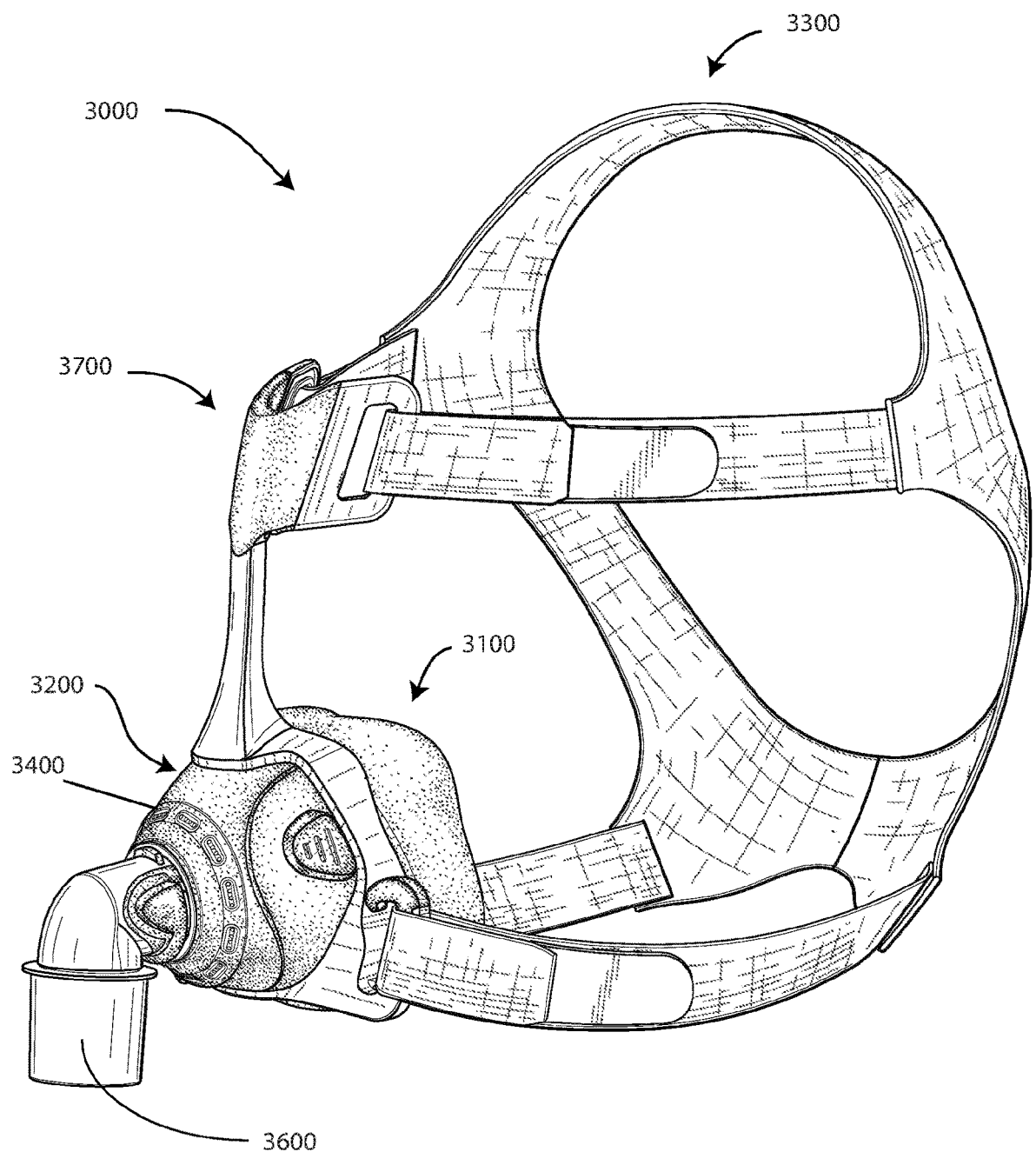
Figure 4A:
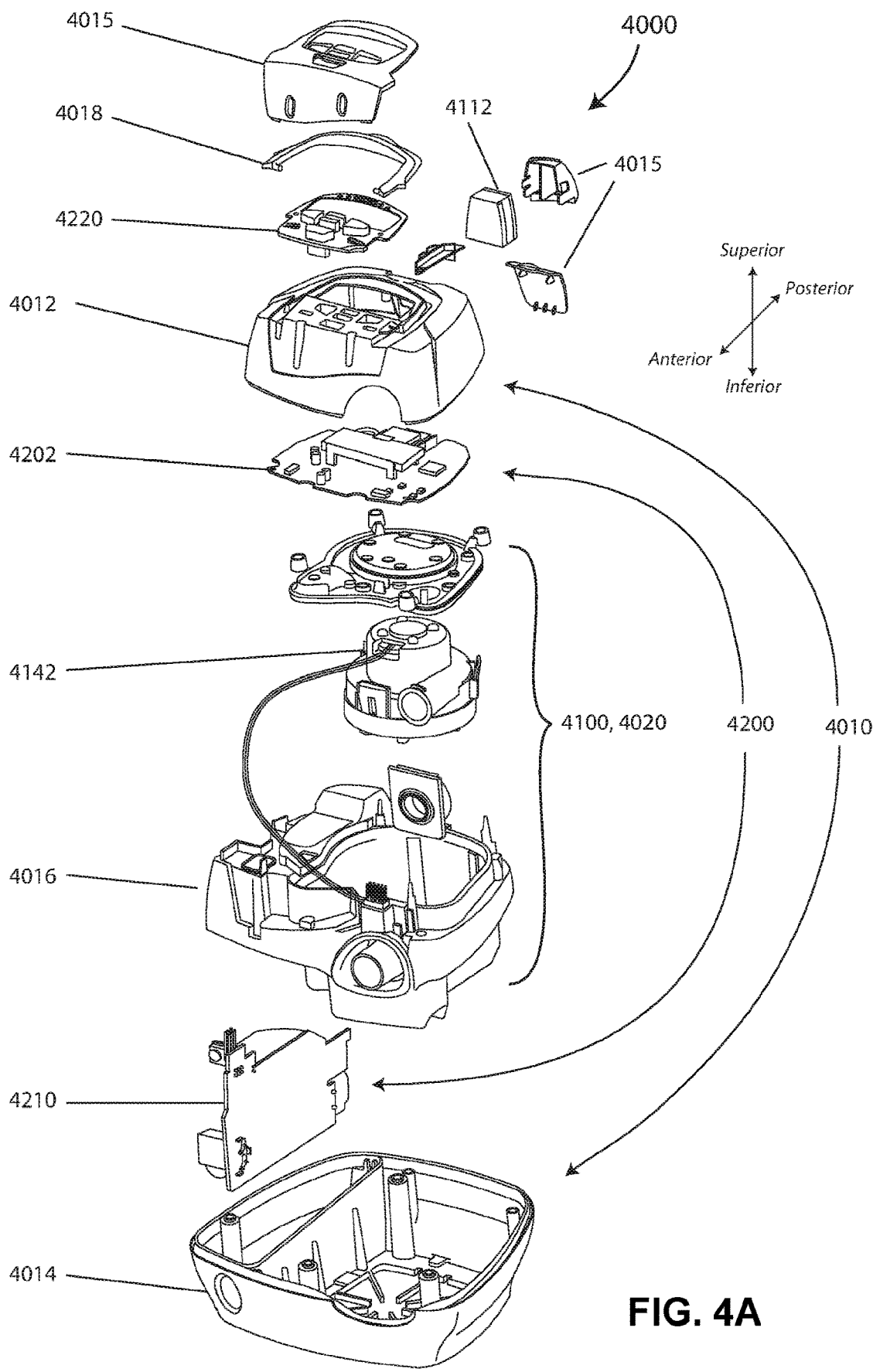
FIG. 4A shows an RPT device in accordance with one form of the present technology.
Figure 4B:
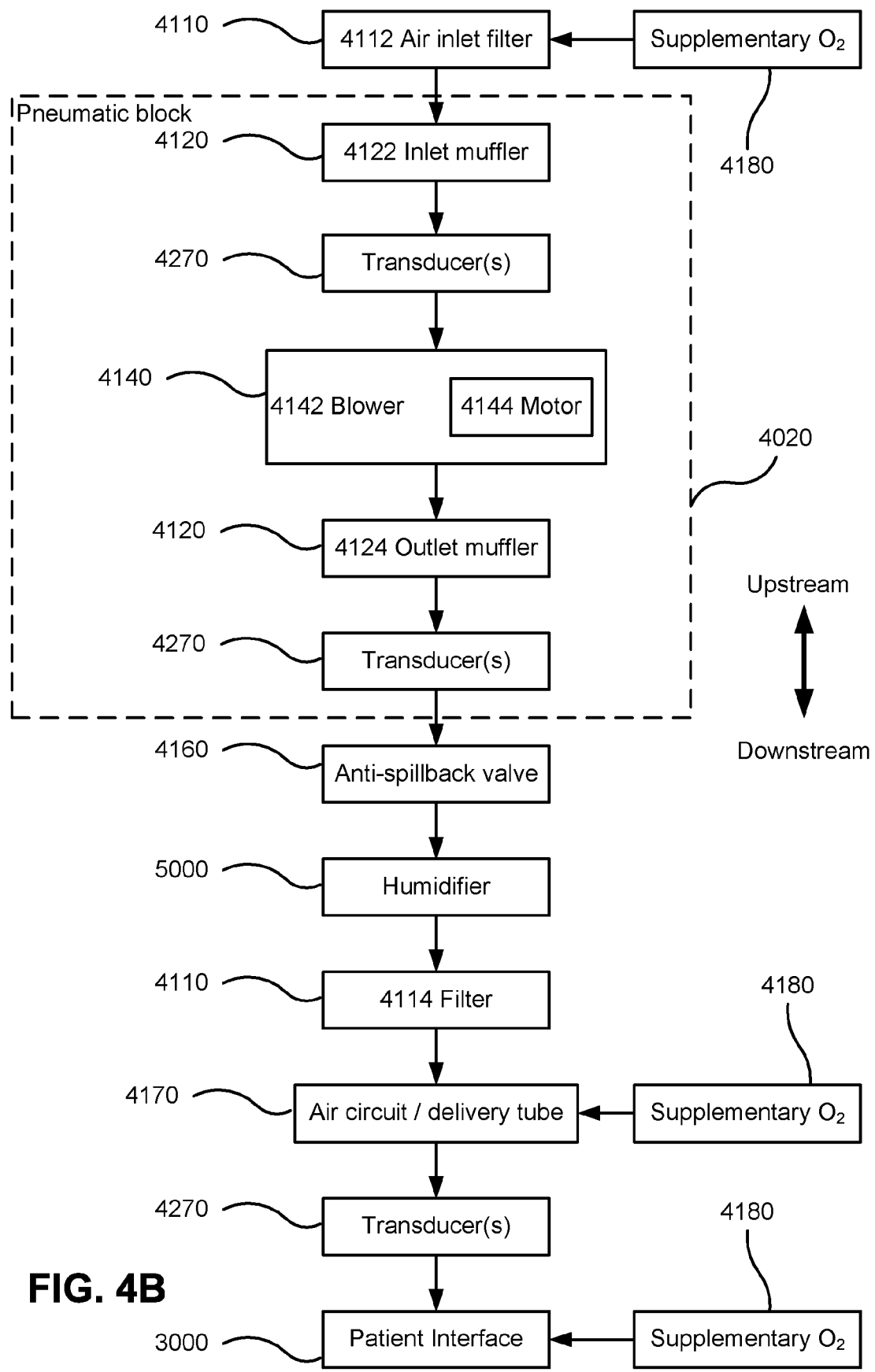
FIG. 4B is a schematic diagram of the pneumatic path of an RPT device in accordance with one form of the present technology. The directions of upstream and downstream are indicated.
Figure 5A:
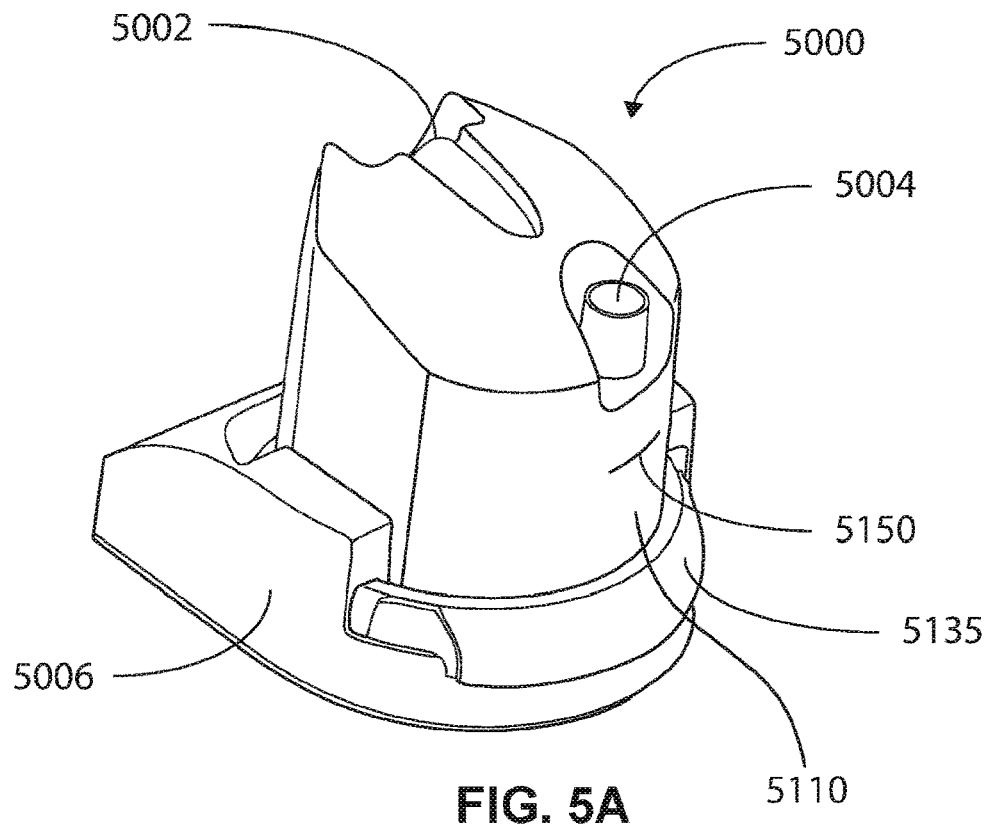

FIG. 5A shows an isometric view of a humidifier in accordance with one form of the present technology.

Figure 5B:
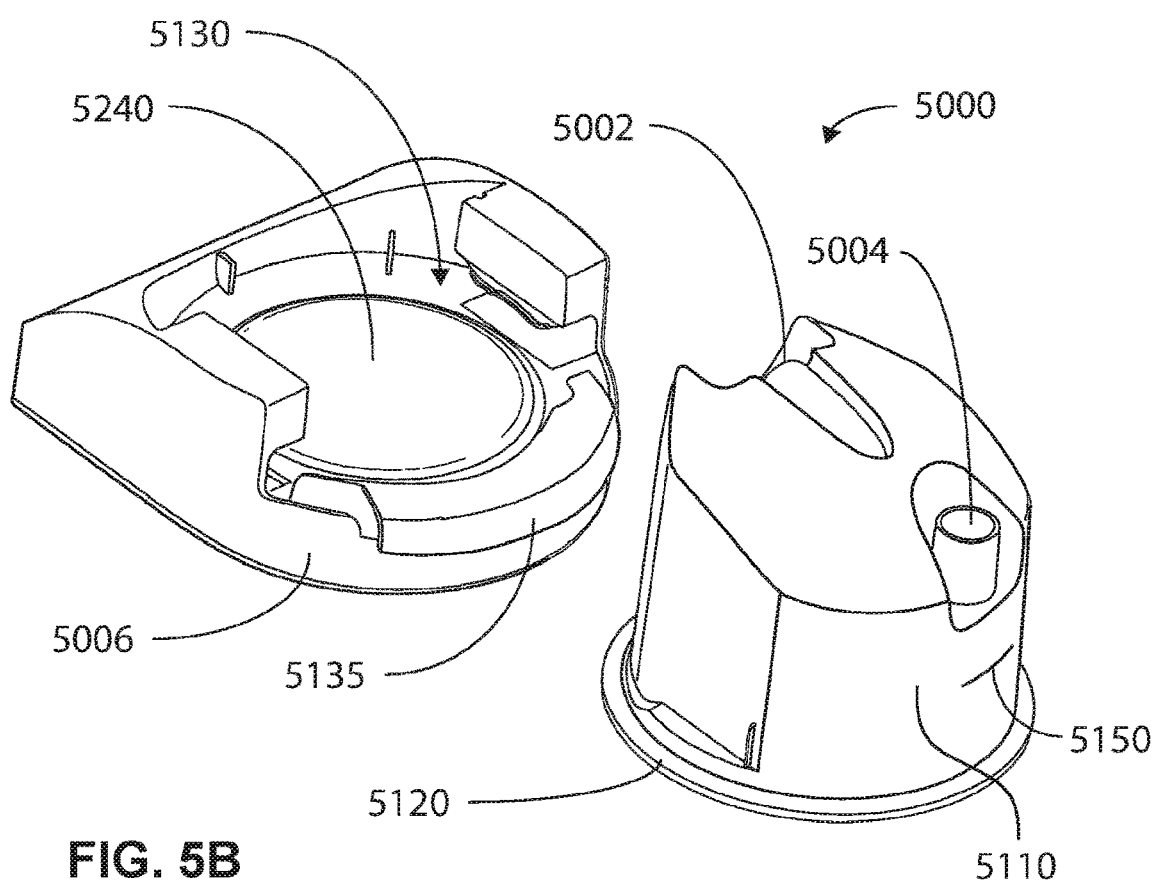

FIG. 5B shows an isometric view of a humidifier in accordance with one form of the present technology, showing a humidifier reservoir 5110 removed from the humidifier reservoir dock 5130.

6.6 Breathing Waveforms

Figure 6A:
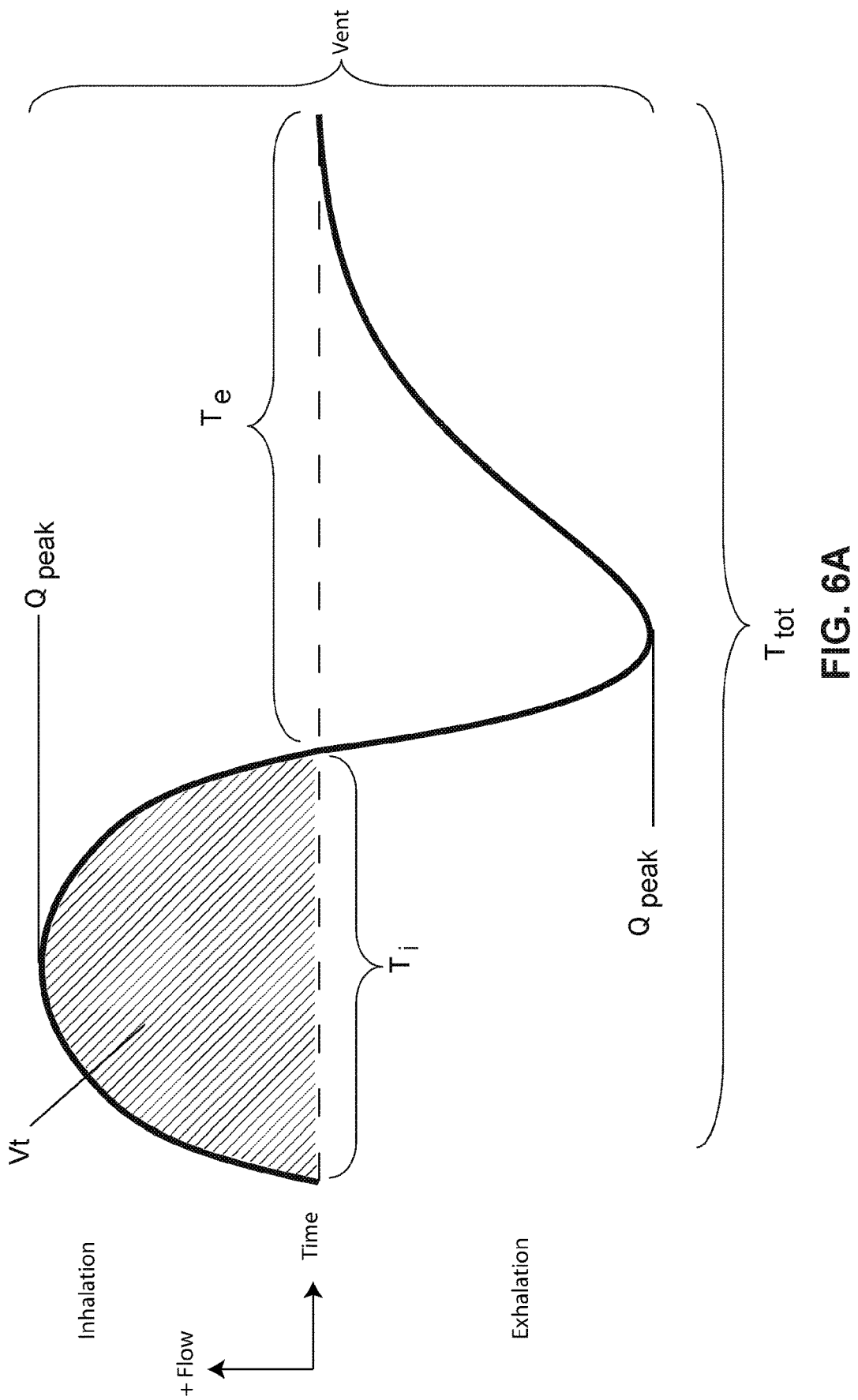

FIG. 6A shows a typical respiratory flow rate waveform of a person while sleeping.

Figure 6B:
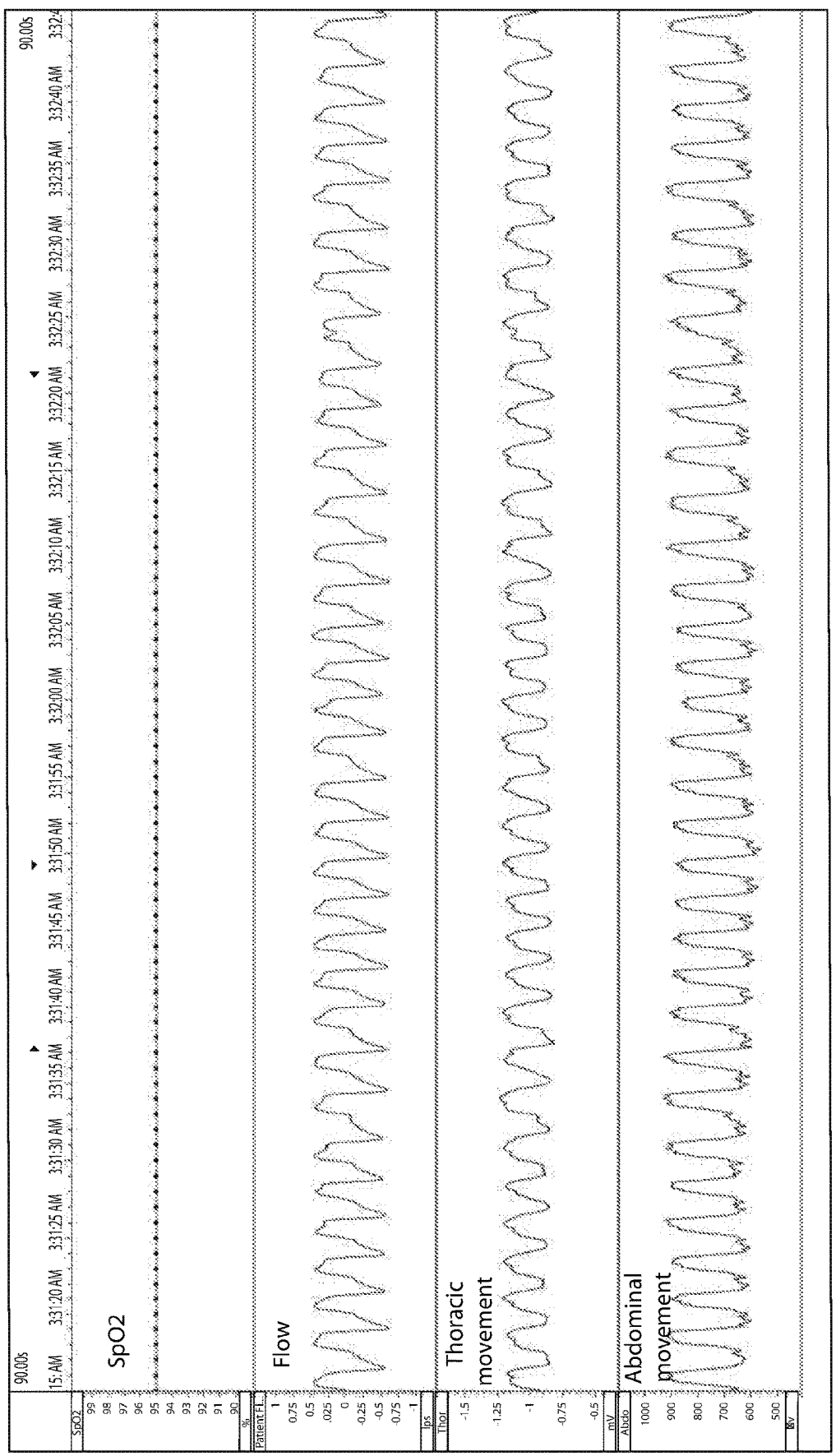

FIG. 6B shows selected polysomnography channels (pulse oximetry, flow rate, thoracic movement, and abdominal movement) of a patient during non-REM sleep breathing normally over a period of about ninety seconds.

6.7 Diagnosis and Monitoring Systems

Figure 7A:
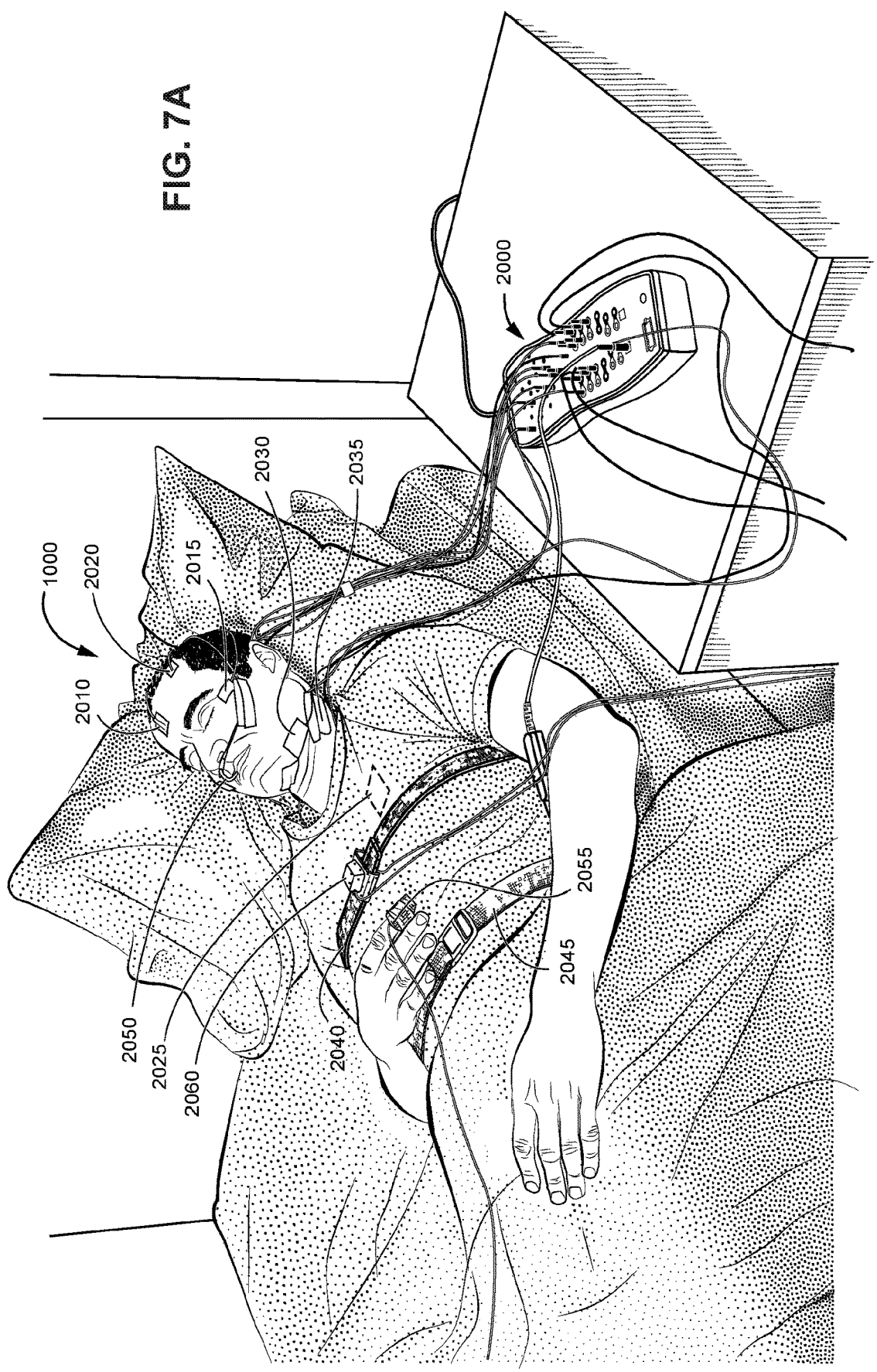

FIG. 7A shows a patient undergoing polysomnography (PSG). The patient is sleeping in a supine sleeping position.

Figure 7B:
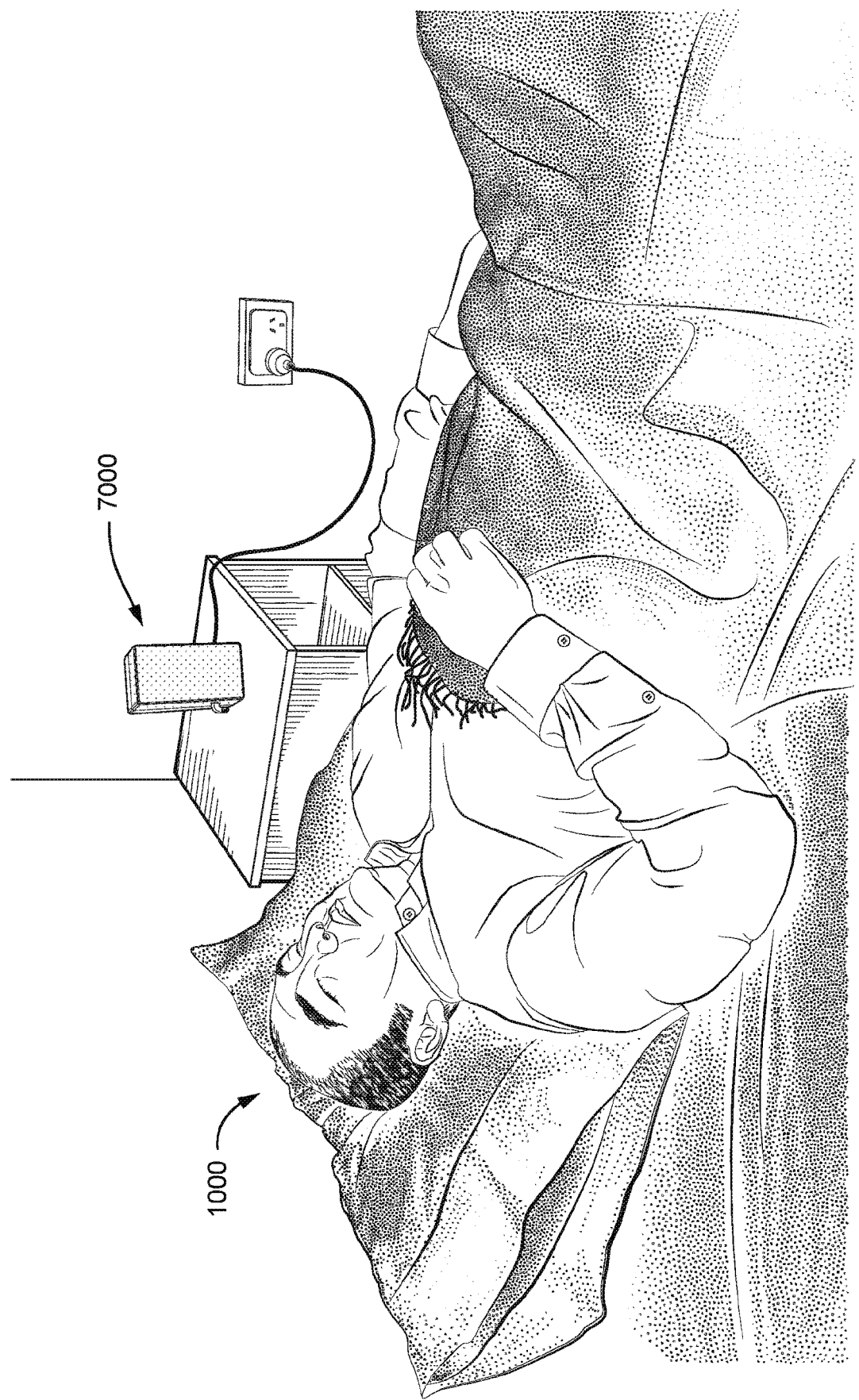

FIG. 7B shows a monitoring apparatus monitoring a sleeping patient in accordance with one form of the present technology.

Figure 7C:
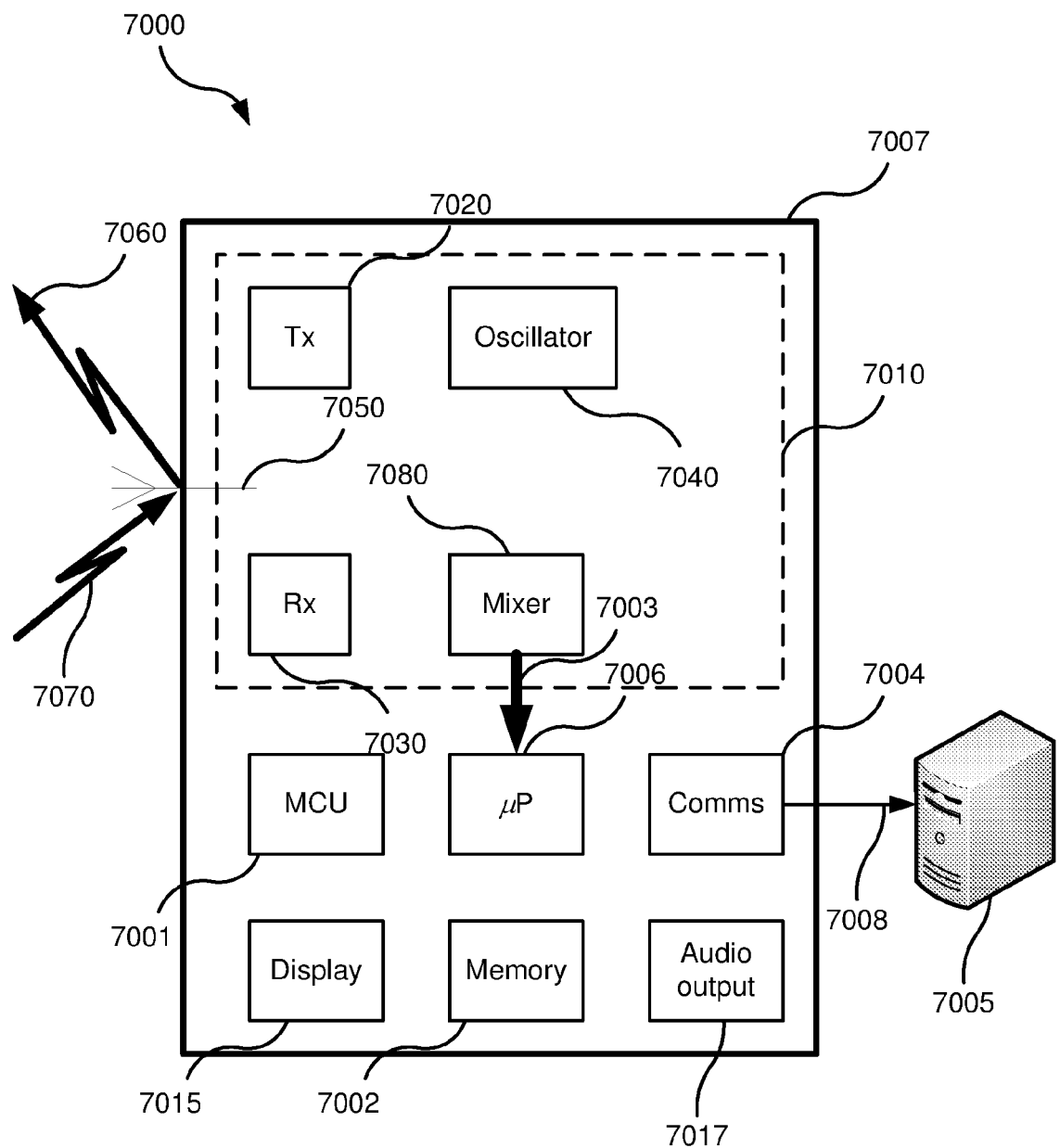

FIG. 7C is a block diagram illustrating the monitoring apparatus of FIG. 7B in more detail.

Figure 8:
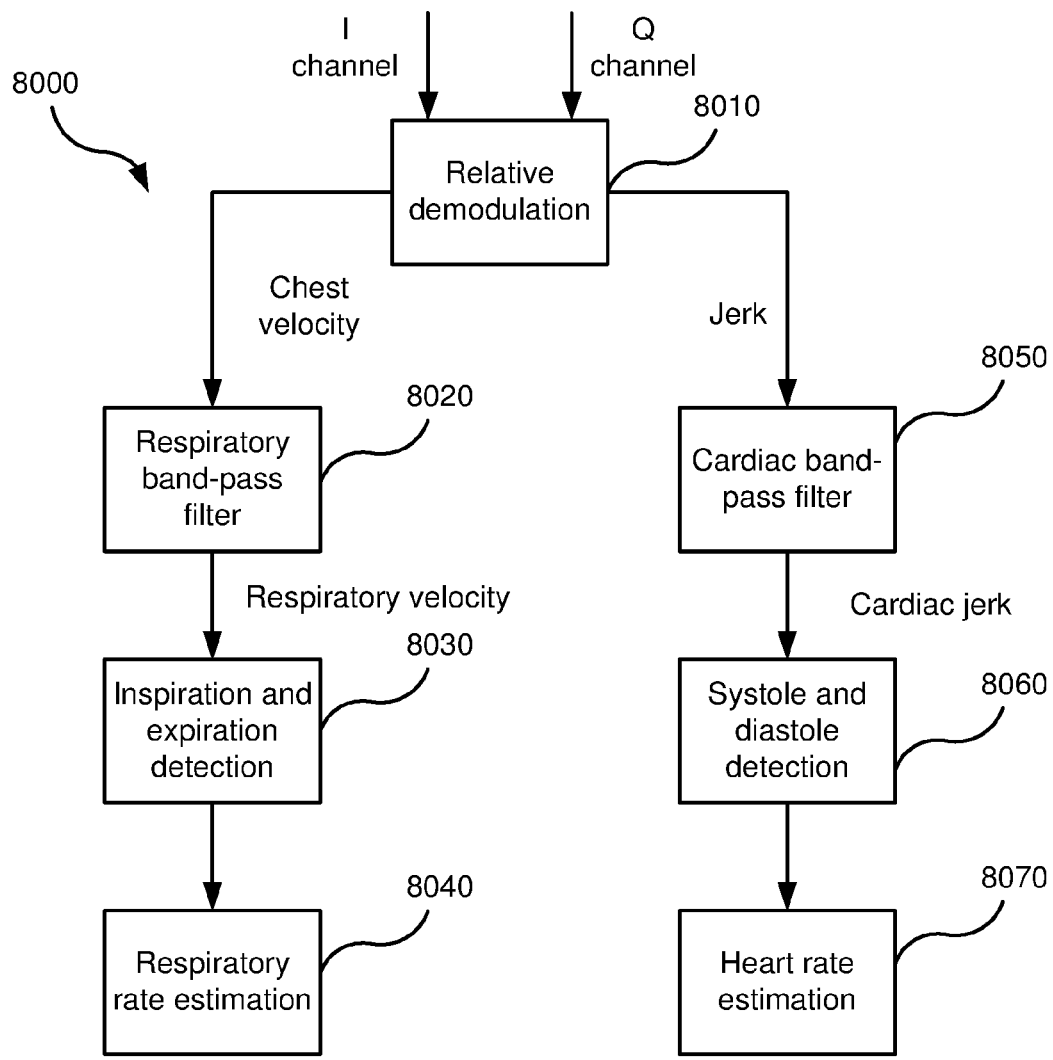

FIG. 8 is a flow chart illustrating a method that may be used to implement an analysis process carried out by the monitoring apparatus of FIG. 7B.

Figure 9:
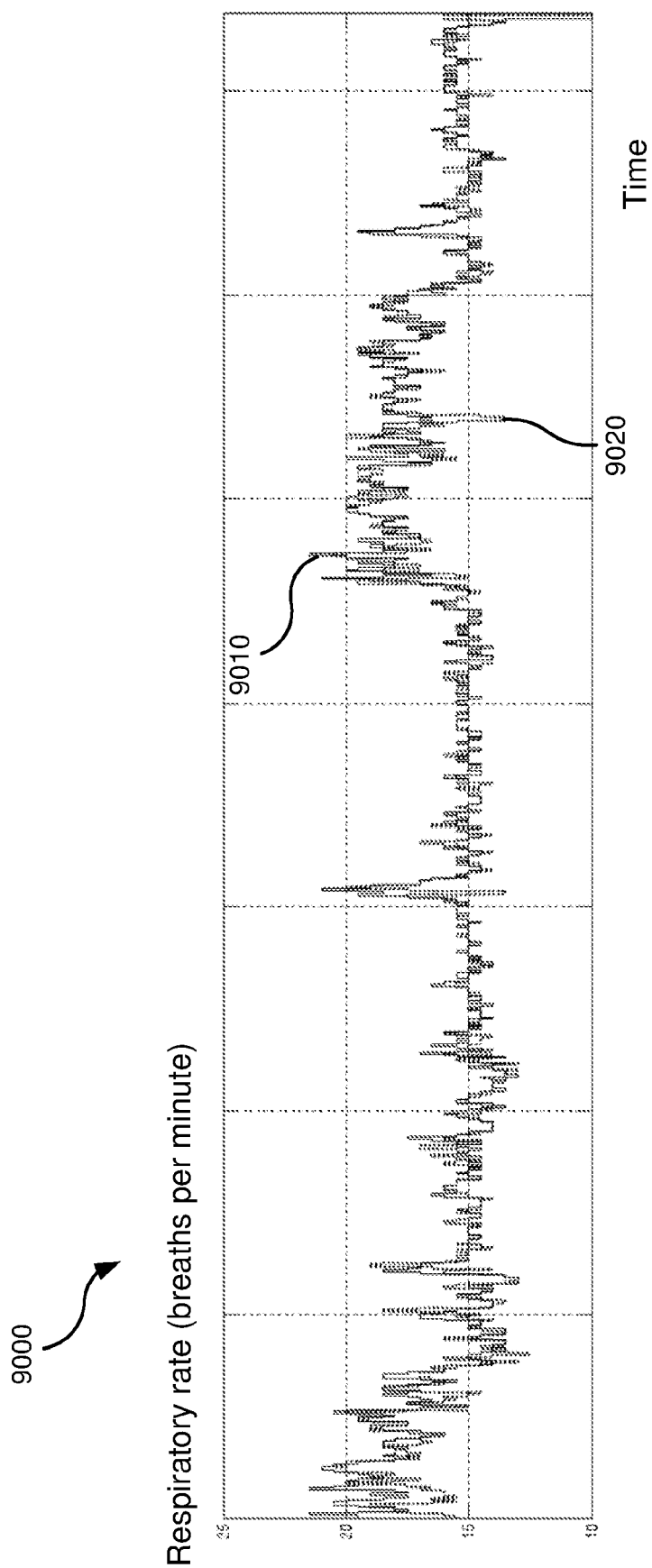

FIG. 9 contains a graph illustrating the performance of the method of FIG. 8 in estimating respiratory rate on example patient data.

Figure 10:
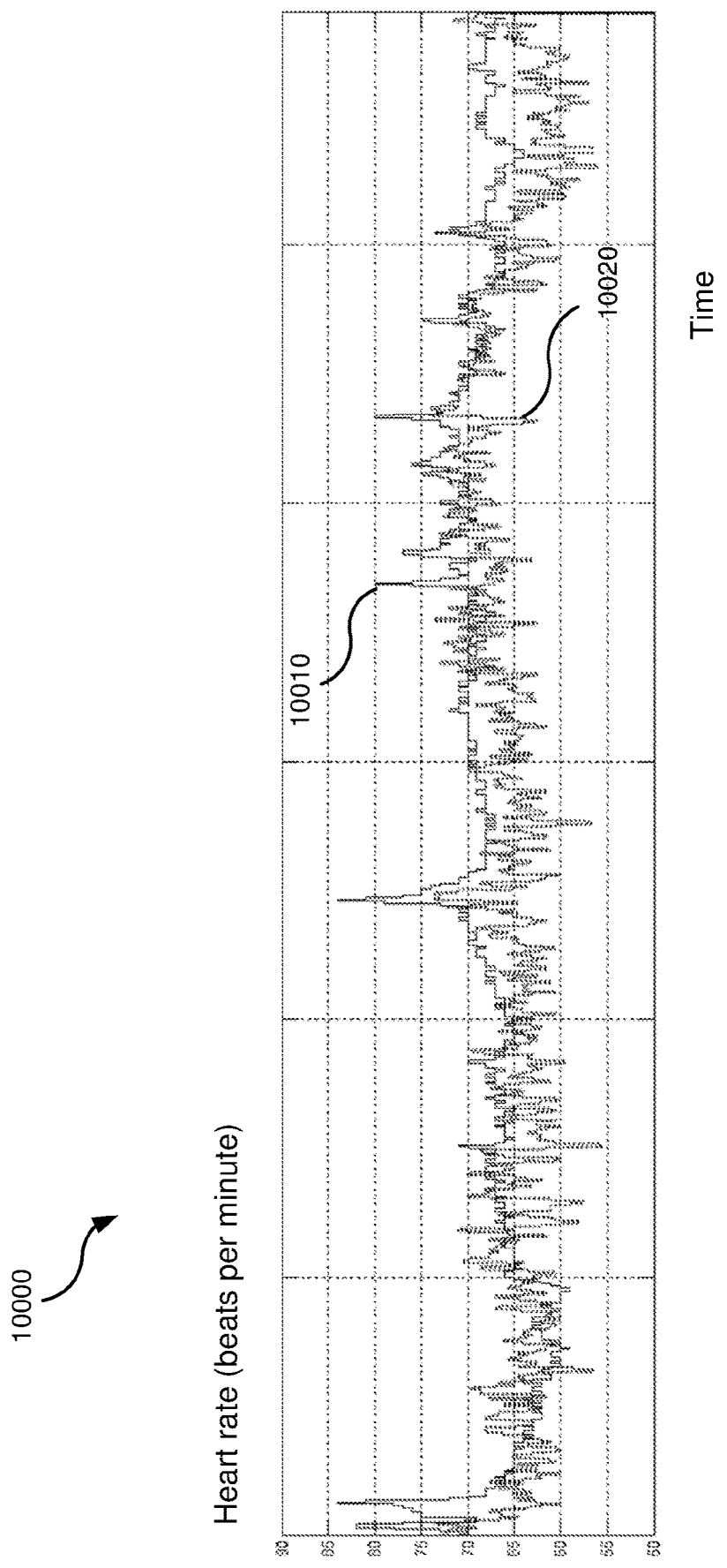

FIG. 10 contains a graph illustrating the performance of the method of FIG. 8 in estimating heart rate on example patient data.

Figure 11:
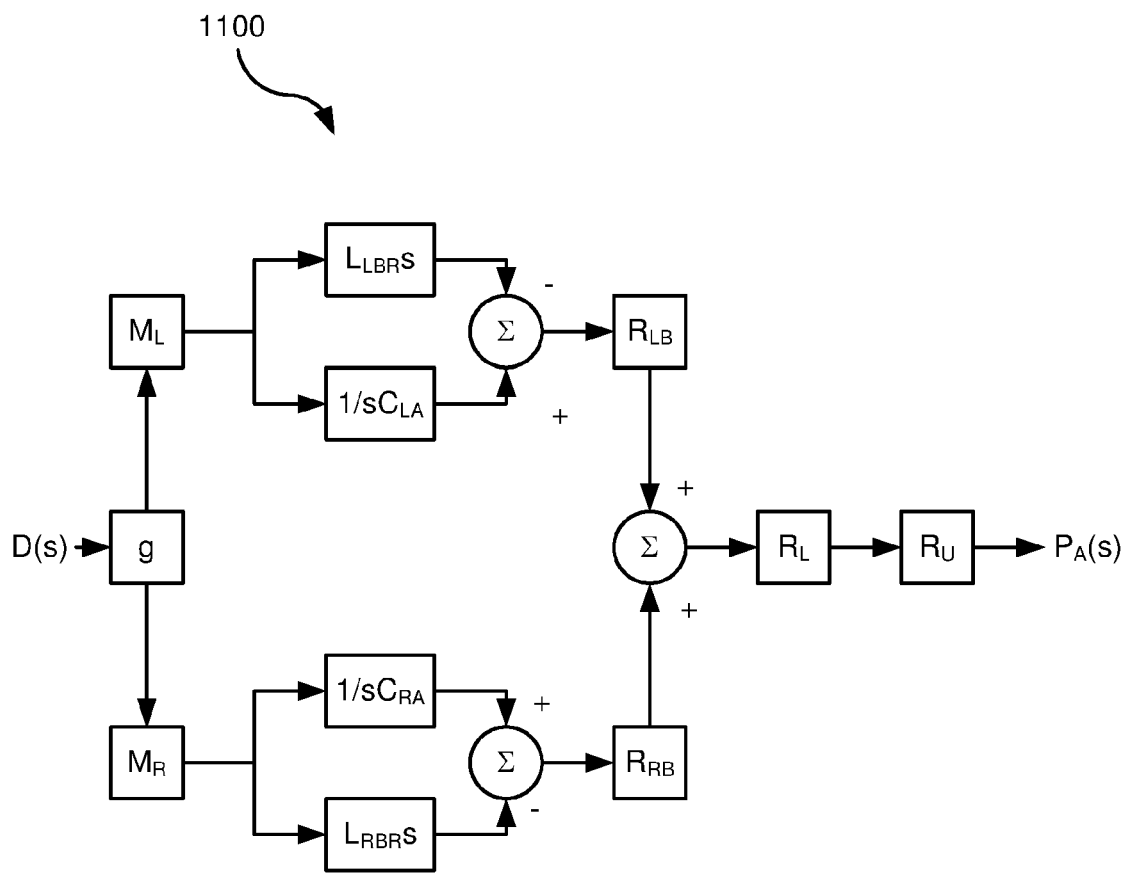

FIG. 11 is a block diagram illustrating a model relating intrapulmonary pressure to chest displacement.

Figure 12:
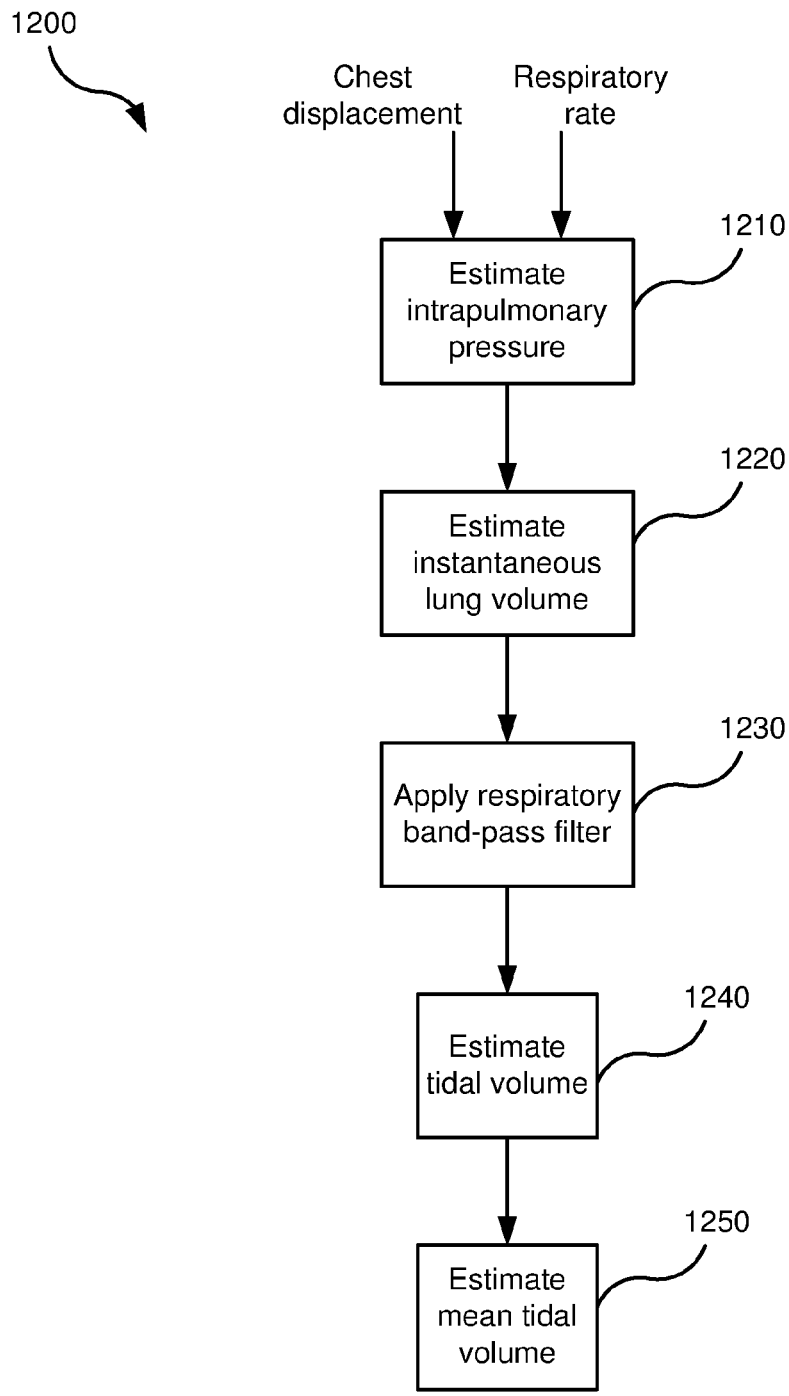

FIG. 12 is a flow chart illustrating a method that may be used to implement an analysis process carried out by the monitoring apparatus of FIG. 7B.

7 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

7.1 THERAPY

In one form, the present technology comprises a method for treating a cardio-respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

7.2 TREATMENT SYSTEMS

In one form, the present technology comprises an apparatus or device for treating a cardio-respiratory disorder. The apparatus or device may comprise an RPT device 4000 for supplying pressurised air to the patient 1000 via an air circuit 4170 to a patient interface 3000.

7.3 PATIENT INTERFACE

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

7.4 RPT DEVICE

An RPT device 4000 in accordance with one aspect of the present technology comprises mechanical, pneumatic, and/or electrical components and is configured to execute one or more algorithms. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

7.5 AIR CIRCUIT

An air circuit 4170 in accordance with an aspect of the present technology is a conduit or a tube constructed and arranged to allow, in use, a flow of air to travel between two components such as RPT device 4000 and the patient interface 3000.

7.6 HUMIDIFIER

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

7.7 BREATHING WAVEFORMS

FIG. 6A shows a model typical breath waveform of a person while sleeping. The horizontal axis is time, and the vertical axis is respiratory flow rate. While the parameter values may vary, a typical breath may have the following approximate values: tidal volume, Vt, 0.5 L, inspiratory time, Ti, 1.6 seconds, peak inspiratory flow rate, Qpeak, 0.4 L/s, expiratory time, Te, 2.4 seconds, peak expiratory flow rate, Qpeak, −0.5 L/s. The total duration of the breath, Ttot, is about 4 seconds. The person typically breathes at a rate of about 15 breaths per minute (BPM), with Ventilation, Vent, about 7.5 L/min. A typical duty cycle, the ratio of Ti to Ttot, is about 40%.

FIG. 6B shows selected polysomnography channels (pulse oximetry, flow rate, thoracic movement, and abdominal movement) of a patient during non-REM sleep breathing normally over a period of about ninety seconds, with about 34 breaths. The top channel shows blood oxygen saturation ($SpO_2$), the scale has a range of saturation from 90 to 99% in the vertical direction. The patient maintained a saturation of about 95% throughout the period shown. The second channel shows quantitative respiratory flow rate, and the scale ranges from −1 to +1 LPS in a vertical direction, and with inspiration positive. Thoracic and abdominal movement are shown in the third and fourth channels.

7.8 MONITORING SYSTEMS 7.8.1 Polysomnography

FIG. 7A shows a patient 1000 undergoing polysomnography (PSG). A PSG system comprises a headbox 2000 which receives and records signals from the following sensors: an EOG electrode 2015; an EEG electrode 2020; an ECG electrode 2025; a submental EMG electrode 2030; a snore sensor 2035; a respiratory inductance plethysmogram (respiratory effort sensor) 2040 on a chest band; a respiratory inductance plethysmogram (respiratory effort sensor) 2045 on an abdominal band; an oro-nasal cannula 2050 with oral thermistor; a photoplethysmograph (pulse oximeter) 2055; and a body position sensor 2060. The electrical signals are referred to a ground electrode (ISOG) 2010 positioned in the centre of the forehead.

7.8.2 Unobtrusive Monitoring Apparatus

One example of a monitoring apparatus 7000 for monitoring the respiration of a sleeping patient 1000 is illustrated in FIG. 7B. The unobtrusive monitoring apparatus 7000 contains a contactless motion sensor generally directed toward the chest of the patient 1000. The motion sensor is configured to generate one or more signals representing chest movement of the patient 1000.

FIG. 7C is a block diagram illustrating the components of the monitoring apparatus 7000 of FIG. 7B in more detail, according to one form of the present technology. In the monitoring apparatus 7000, a contactless sensor unit 7007 includes a contactless motion sensor 7010 generally directed toward the patient 1000. The motion sensor 7010 is configured to generate one or more signals representing chest movement of the patient 1000, from which may be derived one or more cardio-respiratory movement signals representing cardio-respiratory movement of the patient. Cardio-respiratory movement of the chest has two components: respiratory movement, and heartbeat-derived movement. The recoil movements of the body that result from contraction of the heart muscle in ejecting blood from the ventricles is referred to as the Cardioballistic Effect. The heart's pumping force propagates through the entire body, however, the cardioballistic effect is most significant at the chest area where the heart is located. The resulting movements, even at the chest, are too small to be seen by the naked eye but can be detected by sensitive motion sensors such as the unobtrusive monitoring apparatus 7000. Unlike the respiratory component, which is generally sinusoidal, the heart pumping is an 'abrupt' action which is caused by the systolic and diastolic cycles of the beating heart.

The sensor unit 7007 may also include a microcontroller unit (MCU) 7001, and a memory 7002 (e.g. a memory card) for recording data. In one implementation, the sensor unit 7007 may include communications circuitry 7004 configured to transfer data to an external computing device 7005, e.g. a local general purpose computer, a remote server, or other processor-controlled treatment device, via a connection 7008. The connection 7008 may be wired or wireless, in which case the communications circuitry 7004 has wireless capability, and may be direct or indirect via a local network or a wide-area network (not shown) such as the Internet.

The sensor unit 7007 includes a processor 7006 that may be configured to process the signals generated by the motion sensor 7010 as described in detail below.

The sensor unit 7007 includes a display device 7015 configured to provide visual feedback to a user. In one implementation, the display device 7015 comprises one or more warning lights (e.g., one or more light emitting diodes). The display device 7015 may also be implemented as a display screen such as an LCD or a touch-sensitive display. Operation of the display device 7015 is controlled by the processor 7006 based on an assessment of the patient's cardio-respiratory health. The display device 7015 may be operated to show information to a user of the monitoring apparatus 7000, such as the patient 1000, or a physician or other clinician. The display device 7015 may also display a graphical user interface for operation of the monitoring apparatus 7000.

The sensor unit 7007 may also include an audio output 7017 configured to provide acoustic feedback to a user under the control of the processor 7006, e.g., a tone whose frequency varies with respiratory rate, or an alarm which sounds when certain conditions are met.

The above descriptions of the visual display 7015 and the audio output 7017 of the monitoring apparatus 7000 apply equally to comparable elements of the external computing device 7005.

User control of the operation of the monitoring apparatus 7000 may be based on operation of controls (not shown) that are sensed by the processor 7006 of the monitoring apparatus 7000.

One example of a sensor unit 7007 is the SleepMinder device manufactured by ResMed Sensor Technologies Ltd, which contains a contactless radio-frequency (RF) motion sensor 7010. The RF motion sensor 7010 processes signals representing transmitted radio-frequency waves and received reflected ones of the transmitted radio-frequency waves. Other examples include the sensors disclosed in United States Patent Application Publication No. US 2015-0216424 and U.S. Provisional Patent Application No. 62/205,129 filed on Aug. 14, 2015, the entire disclosures of which is incorporated herein by reference.

In one form of the present technology, such as when the SleepMinder device is used as the sensor unit 7007, the motion sensor 7010 includes an RF transmitter 7020 configured to transmit an RF signal 7060. The transmitted signal 7060 for example has the form $$s(t) = u(t)\cos(2\pi f_c t + \theta) \quad \text{(Eq. 1)}$$

In Eq. 1, the carrier frequency is $f_c$ (typically in the range 100 MHz to 100 GHz, e.g. 3 GHz to 12 GHz, e.g. 5.8 GHz or 10.5 GHz), t is time, $\theta$ is an arbitrary phase angle, and u(t) is a pulse shape. In a continuous wave system, the magnitude of u(t) may be unitary, and can be omitted from Eq. 1. More generally, the pulse u(t) may be defined as in Eq. 2:

$$u(t) = \begin{cases} 1, & t \in [kT, kT + T_p], k \in Z \\ 0, & \text{otherwise} \end{cases} \quad \text{(Eq. 2)}$$

where T is the period width, and $T_p$ is the pulse width. Where $T_p \ll T$, this becomes a pulsed continuous wave system. In one case, as $T_p$ becomes very small, the spectrum of the emitted signal becomes very wide, and the system is referred to as an ultra-wideband (UWB) radar or impulse radar. Alternatively, the carrier frequency of the RF transmitted signal 7060 can be varied (chirped) to produce a so-called frequency modulated continuous wave (FMCW) system.

The radio-frequency signal 7060 may be generated by the transmitter 7020 using a local oscillator 7040 coupled with circuitry for applying the pulse gating. In the FMCW case, a voltage-controlled oscillator is used together with a voltage-frequency converter to produce the RF signal 7060 for transmission. The coupling of the transmitted RF signal 7060 to the air may be accomplished using an antenna 7050. The antenna 7050 can be omnidirectional (transmitting power more or less equally in all directions) or directional (transmitting power preferentially in certain directions). It may be advantageous to use a directional antenna 7050 in the apparatus 7000 so that transmitted and reflected energy are primarily coming from one direction. In one implementation of the apparatus 7000, a single antenna 7050 is used for both the transmitter 7020 and the receiver 7030, with a single carrier frequency. Alternatively, multiple receive and transmit antennas 7050 can be used, with multiple carrier frequencies.

The apparatus 7000 is compatible in various embodiments with various types of antenna 7050 such as simple dipole antennas, patch antennas, and helical antennas, and the choice of antenna can be influenced by factors such as the required directionality, size, shape, or cost. It should be noted that the apparatus 7000 can be operated in a manner which has been shown to be safe for human use. The apparatus 7000 has been demonstrated with a total system emitted average power of 1 mW (0 dBm) and lower. The recommended safe power density level for RF exposure is 1 mW/cm². At a distance of 1 metre from a system transmitting at 0 dBm, the equivalent power density will be at least 100 times less than this recommended limit.

In use, the transmitted RF signal 7060 is reflected off objects that reflect radio waves (such as the air-body interface of the patient 1000), and some of the reflected signal 7070 will be received at a receiver 7030, which can be collocated with the transmitter 7020, or which can be separate from the transmitter 7020, in a so-called "bistatic" configuration. The received signal 7070 and the transmitted signal 7060 can be multiplied together in a mixer 7080 (either in an analog or digital fashion). This mixer 7080 can be of the form of a multiplier (as denoted below in (Eq. 3)) or in a circuit which approximates the effect of a multiplier (e.g., an envelope detector circuit which adds sinusoidal waves). For example, in the CW case, the mixed signal will equal $$m(t) = \gamma \cos(2\pi f_c t)\cos(2\pi f_c t + \phi(t)) \quad \text{(Eq. 3)}$$

where $\phi(t)$ is a phase term resulting from the path difference of the transmitted and received signals 7060 and 7070 (in the case where the reflection is dominated by a single reflective object), and $\gamma$ is the attenuation experienced by the reflected signal 7070. If the reflecting object is fixed, then $\phi(t)$ is fixed. In the apparatus 7000, the reflecting object (e.g., the chest wall of the patient 1000) is in general moving, and $\phi(t)$ will be time-varying. As a simple example, if the chest wall is undergoing only a sinusoidal respiratory movement of frequency $f_m$, then the mixed signal m(t) contains a component at $f_m$ (as well as a component centred at $2f_c$ which can be removed by low-pass filtering, e.g. at 1.6 Hz). The signal at the output of the low-pass filter after mixing is referred to as the baseband signal 7003, and in general represents bodily movement of the patient 1000. In some implementations, the mixer 7080 contains an analog-to-digital converter at its output, so the baseband signal 7003 may be a discrete signal (sequence of samples), e.g. with sampling rate equal to 16 Hz.

The amplitude of the baseband signal 7003 is affected by the mean path distance of the reflected signal, leading to detection nulls and peaks in the motion sensor 7010 (i.e. areas where the motion sensor 7010 is less or more sensitive). This effect can be minimised by using quadrature techniques in which the transmitter 7020 simultaneously transmits a signal 90 degrees out of phase (in quadrature) with the signal 7060 of Eq. 1. This results in two reflected signals, both of which can be mixed and low-pass filtered by the mixer 7080, leading to two signals representative of bodily movement, referred to as the "I (in-phase) channel" and the "Q (quadrature) channel". The baseband signal 7003 may comprise one or both of these channels.

In this way, the motion sensor 7010, e.g., a radio-frequency sensor, can observe the movement of the part of the body of the patient 1000 toward which the motion sensor 7010 is directed, e.g. the chest.

As mentioned above, the received signal 7070 can include large non-cardio-respiratory components, e.g. as the result of gross bodily movement. This is due to the fact that the reflected signals from the body can contain more than one reflection path, and lead to complex signals (for example if one hand is moving towards the sensor, and the chest wall is moving away). The reception of such signals is useful as it can indicate that the upper body is in motion, which is useful in determining sleep state.

In order to improve the quality of the chest movement signal, and more general bodily movement signals, the physical volume from which reflected energy is collected by the sensor unit 7007 can be restricted using various methods. For example, the sensor unit 7007 can be made "directionally selective" (that is, it transmits more energy in certain directions), as can the antenna of the receiver 7030. Directional selectivity can be achieved using directional antennas 7050, or multiple RF transmitters 7020. In alternative forms of the present technology, a continuous wave, an FMCW, or a UWB radar is used to obtain similar signals. A technique called "time-domain gating" can be used to only measure reflected signals 7070 which arise from signals at a certain physical distance from the sensor unit 7007. Frequency domain gating (filtering) can be used to ignore motions of the reflected object above a certain frequency.

In implementations of the apparatus 7000 using multiple frequencies (e.g., at 500 MHz and 5 GHz), the lower frequency can be used to determine large motions accurately without phase ambiguity, which can then be subtracted from the higher-frequency sensor signals (which are more suited to measuring small motions). Using such a sensor unit 7007, the apparatus 7000 collects information from the patient 1000, and uses that information to determine chest movement information.

The baseband signal 7003 may be stored in memory 7002 of the sensor unit 7007, and/or transmitted over a link (e.g., connection 7008) for storage in the external computing device 7005, for each monitoring session. In one implementation, each monitoring session is one night in duration.

The processor 7006 of the sensor unit 7007, or that of the external computing device 7005, may analyse the stored baseband signal 7003 according to an analysis process such as those described in detail below. The instructions for the described processes may be stored on a computer-readable storage medium, e.g. the memory 7002 of the sensor unit 7007, and interpreted and executed by a processor, e.g. the processor 7006 of the sensor unit 7007.

7.8.3 Baseband Signal Analysis

One aspect of the present technology comprises one or more analysis processes to obtain cardio-respiratory parameters from a signal representing chest movement of the patient 1000.

In the form of the present technology in which the monitoring apparatus is the unobtrusive monitoring apparatus 7000 illustrated in FIG. 7B and the analysed signal is the baseband signal 7003, an analysis process may be implemented by the processor 7006 of the contactless sensor unit 7007, configured by instructions stored on computer-readable storage medium such as the memory 7002. The results of the analysis, i.e. the cardio-respiratory parameters, may be transmitted to the external computing device 7005 via the connection 7008 as described above.

Alternatively, a processor of the external computing device 7005 may implement all or part of each described analysis process, having obtained the required data, either raw or partly analysed, from the sensor unit 7007 and any other sensors in the apparatus 7000 via the connection 7008 as described above.

In one example, the external computing device 7005 is a clinician-accessible device such as a patient monitoring device that allows a clinician to review the cardio-respiratory parameters, whether these are received from the monitoring apparatus 7000 or obtained by the external computing device 7005 itself. In this example, a database may also be provided to record the cardio-respiratory parameters. Through such an external computing device 7005, a clinician may monitor the patient's cardio-respiratory disorder and issue a report or alert that the patient may require closer observation or hospitalisation.

7.8.3.1 Respiratory Rate and Heart Rate Estimation

FIG. 8 contains a flow chart illustrating a method 8000 that may be used to implement an analysis process mentioned above. The cardio-respiratory parameters obtained by the method 8000 from the I and Q channels of the baseband signal 7003 are respiratory rate and heart rate. As mentioned above, the method 8000 may be carried out by the processor 7006 of the unobtrusive monitoring apparatus 7000 or a processor of the external computing device 7005 in communication therewith. Thus, the steps of the process may be implemented in one or more processors.

The method 8000 starts at step 8010, which performs "relative demodulation" on the I and Q channels to generate two discrete specific motion signals: chest velocity (written herein as v[n]) and "jerk" (written herein as j[n]). The chest velocity signal v[n] is the discrete first derivative of the chest displacement d[n]. The jerk motion signal j[n] is the discrete third derivative of the chest displacement d[n]. The relative demodulation step 8010 will be described in more detail below.

Steps 8020 to 8040 are then carried out on the chest velocity signal v[n]. Step 8020 applies a respiratory band-pass filter (RBPF) $h_r[n]$ to the velocity v[n] to extract the respiratory velocity x'[n], which is the discrete derivative of the component x[n] of the chest displacement that is due to respiration. In one implementation, the RBPF is a sixth-order Butterworth band-pass filter with unity gain. One reason for choosing such a Butterworth filter is that the frequency response of a Butterworth filter is maximally flat (i.e. has no ripples) in the pass-band and rolls off towards zero in the stop-band. In addition, the implementation of a Butterworth filter is much simpler and performs much faster as compared to other finite impulse response (FIR) filters, which is more suitable for implementation on the unobtrusive monitoring apparatus 7000. In one such implementation, the pass-band for the RBPF is 0.2-0.5 Hz, corresponding to a respiratory rate of 12-30 breaths per minute.

Step 8030 then detects the inspiration and expiration phases of respiration from the respiratory velocity x'[n]. The inspiration and expiration phases are represented by binary inspiration and expiration signals i[n] and e[n].

The inspiration signal i[n] is set to one at negative-going zero-crossings of the respiratory velocity x'[n], which coincide with positive peaks of the respiratory displacement x[n].

$$i[n] = \begin{cases} 1, & x'[n] \leq 0 \wedge x'[n-1] > 0 \wedge R_{1i} \wedge R_{2i} \\ 0, & \text{otherwise} \end{cases} \quad (\text{Eq. 4})$$

$R_{1i}$ is an indicator function that is equal to one when the current index n minus the index n' of the previously detected inspiration (i.e. the value of n when i[n] was last equal to one) is greater or equal to $2f_s$. This prevents zero-crossings from being detected with a spacing of less than two seconds, corresponding to a maximum permissible breathing rate of 30 breaths per minute.

$R_{2i}$ is an indicator function that is equal to one when the current index n minus the index n' of the previously detected expiration (i.e. the value of n when e[n] was last equal to one) is greater or equal to $f_s$. This prevents negative-going zero-crossings from being detected with a spacing of less than one second from positive-going zero-crossings, corresponding to a maximum permissible breathing rate of 30 breaths per minute.

The expiration signal e[n] is set to one at positive-going zero-crossings of the respiratory velocity x'[n], which coincide with negative peaks of the respiratory displacement x[n].

$$e[n] = \begin{cases} 1, & x'[n] \geq 0 \wedge x'[n-1] < 0 \wedge R_{1e} \wedge R_{2e} \\ 0, & \text{otherwise} \end{cases} \quad (\text{Eq. 5})$$

$R_{1e}$ is an indicator function that is equal to one when the current index n minus the index n' of the previously detected expiration (i.e. the value of n when e[n] was last equal to one) is greater or equal to $2f_s$.

$R_{2e}$ is an indicator function that is equal to one when the current index n minus the index n' of the previously detected inspiration (i.e. the value of n when i[n] was last equal to one) is greater or equal to $f_s$.

Finally, step 8040 estimates the respiratory rate (RR) from the binary inspiration and expiration signals i[n] and e[n]. The respiratory rate can be estimated as the average number of detected inspiration and expiration phases (negative- and positive-going zero-crossings of respiratory velocity x'[n] respectively) in a window divided by the window width. In one implementation, a fixed window of width 60 seconds (2 epochs) and a sliding window of width 30 seconds (1 epoch) are employed in step 8040 for respiratory rate estimation.

Optionally, step 8040 may also return the inspiratory time Ti and expiratory time Te of each breath from the durations between adjacent negative- and positive-going zero-crossings indicated by the inspiration and expiration signals i[n] and e[n].

Steps 8050 to 8070 are then carried out on the jerk signal j[n]. The reason for using jerk to detect heart rate is that the abrupt heartbeat-related component of chest movement is emphasised by each differentiation. That is, each time the chest displacement signal is differentiated, the "slow" motions in the signal get reduced, while the amplitude of "faster" motions is increased. The jerk signal j[n] therefore already has the heartbeat-related component foregrounded. Step 8050 applies a cardiac band-pass filter (CBPF) $h_c[n]$ to the jerk j[n] to extract the cardiac jerk y'''[n], which is the discrete third derivative of the component y[n] of the chest displacement that is due to the heart beating. In one implementation, the CBPF is a sixth-order Butterworth band-pass filter with unity gain. One reason for choosing such a Butterworth filter is that the frequency response of a Butterworth filter is maximally flat (i.e. has no ripples) in the pass-band and rolls off towards zero in the stop-band. In addition, the implementation of a Butterworth filter is much simpler and performs much faster as compared to other FIR filters, which is more suitable for implementation on the unobtrusive monitoring apparatus 7000. In one such implementation, the pass-band for the CBPF is 0.7-1.6 Hz, corresponding to a heart rate of 42-96 beats per minute.

Step 8060 then detects the systole and diastole phases of each heartbeat from the cardiac jerk y'''[n]. The systole and diastole phases are represented by binary systole and diastole signals s[n] and d[n].

The systole signal s[n] is set to one at negative-going zero-crossings of the cardiac jerk y'''[n], which coincide with positive peaks of the cardiac displacement y[n].

$$s[n] = \begin{cases} 1, & y'''[n] \leq 0 \wedge y'''[n-1] > 0 \wedge C_{1s} \wedge C_{2s} \\ 0, & \text{otherwise} \end{cases} \quad (\text{Eq. 6})$$

$C_{1s}$ is an indicator function that is equal to one when the current index n minus the index n' of the previously detected systole (i.e. the value of n when s[n] was last equal to one) is greater or equal to $0.5f_s$, where $f_s$ is the sampling rate. This prevents zero-crossings from being detected with a spacing of less than half a second, corresponding to a maximum permissible heart rate of 120 beats per minute.

$C_{2s}$ is an indicator function that is equal to one when the current index n minus the index n' of the previously detected diastole (i.e. the value of n when d[n] was last equal to one) is greater or equal to $0.25f_s$. This prevents negative-going zero-crossings from being detected with a spacing of less than 0.25 seconds from positive-going zero-crossings, corresponding to a maximum permissible heart rate of 120 breaths per minute.

The diastole signal d[n] is set to one at positive-going zero-crossings of the cardiac jerk y'''[n], which coincide with negative peaks of the cardiac displacement y[n].

$$d[n] = \begin{cases} 1, & y'''[n] \geq 0 \wedge y'''[n-1] < 0 \wedge C_{1d} \wedge C_{2d} \\ 0, & \text{otherwise} \end{cases} \quad (\text{Eq. 7})$$

$C_{1d}$ is an indicator function that is equal to one when the current index n minus the index n' of the previously detected diastole (i.e. the value of n when d[n] was last equal to one) is greater or equal to $0.5f_s$.

$C_{2d}$ is an indicator function that is equal to one when the current index n minus the index n' of the previously detected systole (i.e. the value of n when s[n] was last equal to one) is greater or equal to $0.25f_s$.

Finally, step 8070 estimates the heart rate (HR) from the binary systole and diastole signals s[n] and d[n]. The heart rate can be estimated as the average number of detected systole and diastole phases (negative- and positive-going zero-crossings of cardiac jerk y'''[n]) in a window divided by the window width. In one implementation, a fixed window of width 60 seconds (2 epochs) and a sliding window of width 30 seconds (1 epoch) are employed in step 8070 for heart rate estimation.

7.8.3.1.1 Relative Demodulation

The name 'relative demodulation' is given to step 8010 as an application of the 'relativity' concept in the demodulation of the patient's chest motion from the I and Q channels. Relative demodulation pivots from conventional displacement and phase-shift demodulation to introduce derivative analysis. Relative demodulation is simple enough to be carried out in real time and provides the following advantages over conventional demodulation:

Eliminates DC offsets, clutter, and null-points.
Approximates the instantaneous derivatives of the patient's periodic chest motions.
Allows separation of the instantaneous respiratory and cardiac chest motions.

Relative demodulation starts from the following expressions for the I and Q channels of the baseband signal 7003:

$$I(t) = V_I + A_I \cos\left(\theta_0 + \frac{4\pi}{\lambda}(d_0 + d(t)) + \Delta\phi(t)\right) \quad \text{(Eq. 8)}$$

$$Q(t) = V_Q + A_Q \sin\left(\theta_0 + \frac{4\pi}{\lambda}(d_0 + d(t)) + \Delta\phi(t)\right) \quad \text{(Eq. 9)}$$

where $\lambda$ is the wavelength of the transmitted RF signal, $V_I$ and $V_Q$ are DC offsets, and $A_I$ and $A_Q$ are received amplitudes. The argument of the cos and sin functions is the phase term $\phi(t)$ from Eq. 3 above. Its components are:

$\theta_0$, the constant phase offset of the system;
$d_0$, a baseline distance from the motion sensor 7010 around which the patient's chest moves;
d(t), the instantaneous chest displacement from the baseline distance, comprising periodic components due to respiration and heartbeat (written as x(t) and y(t) respectively), and a non-periodic component due to gross bodily movement; and
$\Delta\phi(t)$, the phase noise of the system.

For cardio-respiratory monitoring using the monitoring apparatus 7000, the distance to the patient's chest is usually within 0.5 to 3.0 metres, which makes the phase noise term $\Delta\phi(t)$ negligible.

The time derivatives of the I and Q channels may be obtained by differentiating Eqs. 8 and 9:

$$I'(t) = -\frac{4\pi}{\lambda} v(t) A_I \sin\left(\theta_0 + \frac{4\pi}{\lambda}(d_0 + d(t))\right) \quad \text{(Eq. 10)}$$

$$Q'(t) = \frac{4\pi}{\lambda} v(t) A_Q \cos\left(\theta_0 + \frac{4\pi}{\lambda}(d_0 + d(t))\right) \quad \text{(Eq. 11)}$$

where v(t) is the derivative of the chest displacement d(t).

In the context of relative demodulation, the I and Q channels are referred to as 'Observer I' and 'Observer Q'. The patient's chest motion is referred to as 'Observation Target'. The fundamental relative demodulation concepts are as follows:

Both 'Observer I' and 'Observer Q' are moving at the same speed, however, at different phases.
The instantaneous derivatives of the 'Observer I' and 'Observer Q' are 'relative to' and 'impacted by' the instantaneous derivatives of the 'Observation Target'.
At any given point in time, both 'Observer I' and 'Observer Q' observe the same 'Observation Target' instantaneous derivatives with respect to the other 'Observer'.

Using Eqs. 10 and 11, the 'Observation Target' instantaneous velocity as observed by 'Observer I' with respect to 'Observer Q' and 'Observer Q' with respect to 'Observer I' can be expressed respectively as:

$$v_I(t) = -\frac{\lambda}{4\pi}\left(\frac{A_Q I'(t)}{A_I (Q(t) - V_Q)}\right) \quad \text{(Eq. 12)}$$

and $$v_Q(t) = \frac{\lambda}{4\pi}\left(\frac{A_I Q'(t)}{A_Q (I(t) - V_I)}\right) \quad \text{(Eq. 13)}$$

The null-points of velocity estimation can be eliminated by averaging the 'Observation Target' instantaneous velocity with respect to 'Observer I' and 'Observer Q'. The resultant 'Observation Target' instantaneous velocity can be expressed as:

$$v(t) = \frac{\lambda}{8\pi}\left(\frac{kQ'(t)}{(I(t) - V_I)} - \frac{I'(t)}{k(Q(t) - V_Q)}\right) \quad \text{(Eq. 14)}$$

where $k = A_I / A_Q$.

The third derivative of displacement, i.e. the second derivative of velocity, referred to as "jerk", describes the changes of acceleration. Therefore, to describe the changes that the cardiac acceleration imposes on the respiratory acceleration, relative demodulation may also derive the resultant 'Observation Target' instantaneous jerk j(t). The 'Observation Target' instantaneous jerk j(t) can be expressed as:

$$j(t) = \frac{d^2}{dt^2} v(t) \quad \text{(Eq. 15)}$$

Backwards-difference numerical approximations may be used for their simplicity in implementation to discretise the continuous-time 'Relative Demodulation' derivatives. The resulting discretised 'Relative Demodulation' equations are as follows:

$$v[n] = \frac{\lambda}{8\pi} f_s \left[\frac{k[Q[n] - Q[n-1]]}{[I[n] - V_I]} - \frac{[I[n] - I[n-1]]}{k[Q[n] - V_Q]}\right] \quad \text{(Eq. 16)}$$

$$j[n] = f_s^2 [v[n] - 2v[n-1] + v[n-2]] \quad \text{(Eq. 17)}$$

The voltage offsets $V_I$ and $V_Q$ are set to half the maximum output value of the analog-to-digital converter at the output of the mixer 7080. In most implementations, the I and Q channel amplitude gain constants $A_I$ and $A_Q$ are approximately equal. Therefore, the ratio k may be set to 1.

7.8.3.1.2 Example Results

The example patient data was obtained from twenty patients with New York Heart Association (NYHA) Heart Failure Classification Class II & III. The patients underwent full PSG, manually scored by sleep experts. A monitoring apparatus similar to the monitoring apparatus 7000 was installed in the PSG laboratory and the I and Q channels were recorded simultaneously with the PSG signals. The monitoring apparatus was placed facing the patient in line with chest at a distance of approximately 0.5 metres and an elevation of approximately 0.5 metres from the edge of the bed.

FIG. 9 contains a graph 9000 illustrating the performance of the method 8000 of FIG. 8 in estimating respiratory rate on a portion of the example patient data. The graph 9000, which shows the analysis results from one of the patient monitoring sessions of duration 6.39 hours, contains two traces. The solid trace 9010 is the respiratory rate estimated from the chest band respiratory effort sensor 2040, and the dotted trace 9020 is the respiratory rate estimated from the I and Q channels using the method 8000. The respiratory rate estimation for the respiratory effort PSG signal was performed using the RBPF, inspiration and expiration detection, and respiratory rate estimation steps 8020, 8030, and 8040 to ensure a fair comparison.

FIG. 10 contains a graph 10000 illustrating the performance of the method 8000 of FIG. 8 in estimating heart rate on a portion of the example patient data. The graph 10000, which shows the analysis results from one of the patient monitoring sessions of duration 6.39 hours, contains two traces. The solid trace 10010 is the heart rate estimated from the ECG 2025, and the dotted trace 10020 is the respiratory rate estimated from the I and Q channels using the method 8000. The ECG heart rate estimation utilized a reliable real-time QRS detection algorithm by Pan-Tompkins [1] to extract the R-wave peaks from the ECG. The heart rate was then calculated from the number of identified R-peaks per selected window.

FIGS. 9 and 10 show that the respiratory rate and heart rate estimated using the method 8000 track exceptionally well with the respiratory effort-estimated respiratory rate and ECG-estimated heart rate respectively for the entire duration of the monitoring session. Across all twenty patients' monitoring sessions, the respiratory rate estimation achieved 91.5% median accuracy compared to the PSG with median error of 1.31 breaths per minute. The heart rate estimation achieved 91.3% median accuracy compared to the PSG with median error of 6.16 beats per minute.

7.8.3.2 Chest Displacement Estimation

An instantaneous chest displacement signal $d[n]$ may be found by numerically integrating the chest velocity signal $v[n]$ produced by the relative demodulation step 8010 of the method 8000. In one implementation using the trapezoidal rule with even spacing, the numerical integration may be implemented as follows:

$$d[n] = d[n-1] + \left[\frac{v[n] + v[n-1]}{2f_s}\right] \quad \text{(Eq. 18)}$$

Alternatively, the instantaneous chest displacement signal $d[n]$ may be computed by numerically integrating the respiratory velocity signal $x'[n]$ produced by the respiratory band-pass filtering step 8020 of the method 8000.

7.8.3.3 Intrapulmonary Pressure and Tidal Volume Estimation

A mathematical model may be derived to define the relationship between the intrapulmonary pressure $p_A(t)$ and the chest displacement $d(t)$. The model may be used, such as in the fashion of a processing function implemented in a processor with one or more inputs, to convert estimates of chest displacement to estimates of intrapulmonary pressure. The model takes an engineering approach with the utilization of electronic circuit-like elements to describe the time-varying differential relationships. The lungs are modelled as containers of certain volume that can hold a certain amount of pressurised air. The resistance and elasticity in the respiratory system may be modelled using a resistor and an inductor. The model is presented in the Laplace transform's s-domain; this is for mathematical convenience in analyzing the time-varying differential parameters.

FIG. 11 is a block diagram illustrating a pulmonary ventilation model 1100 relating intrapulmonary pressure $P_A(s)$ to chest displacement $D(s)$. The descriptions of the variables used in FIG. 11 are as follows:

g—standard gravitational constant (9.8 ms$^{-2}$).

$M_L$ and $M_R$—The mass portion of the patient's body mass (in kg) residing in the left and right chest area.

$C_{LA}$ and $C_{RA}$—the left and right lung volumes.

$L_{LBR}$ and $L_{RBR}$—the left and right bronchiole and terminal bronchiole elasticity, which cause changes in resistance due to changes in gas pressure.

$R_{LB}$ and $R_{RB}$—the left and right secondary and tertiary bronchus resistance.

$R_L$—the larynx and trachea resistance.

$R_U$—the upper respiratory system airway resistance, including the nose, pharynx & associated structures.

The following assumptions may be applied to the pulmonary ventilation model 1100 illustrated in FIG. 11:

The left lung volume is approximately equal to the right lung volume, denoted by $C_A$.

The left bronchiole and terminal bronchiole elasticity are approximately equal to the right bronchiole and terminal bronchiole elasticity, denoted by $L_{BR}$.

The left secondary and tertiary bronchus resistance is approximately equal to the right secondary and tertiary bronchus resistance, denoted by $R_B$.

From the pulmonary ventilation model 1100 illustrated in FIG. 11, applying the above assumptions, the following transfer function relating intrapulmonary pressure $P_A(s)$ to chest displacement $D(s)$ may be derived:

$$\frac{P_A(s)}{D(s)} = -K\left(\frac{s^2 - k_1}{s}\right) \quad \text{(Eq. 19)}$$

where $$K = g(M_L + M_R)R_L R_U R_B L_{BR} \quad \text{(Eq. 20)}$$

and $$k_1 = \frac{1}{L_{BR} C_A} \quad \text{(Eq. 21)}$$

The negative sign on the coefficient K in Eq. 19 indicates that when the lung volume increases due to the contraction of the diaphragm, which results in the increase of the chest displacement, the intrapulmonary pressure decreases for inspiration to occur, and vice versa for expiration.

The product of coefficients $L_{BR}$ and $C_A$ in the denominator of $k_1$ in Eq. 21 can be seen as a time constant ($\tau$), which is the period of the pressure accumulation in the alveoli. The reciprocal of $\tau$, i.e. $k_1$, is therefore the respiratory rate in Hertz, which may be computed as the respiratory rate (RR) in breaths per minute divided by 60 seconds.

The $s^2$ term in Eq. 19 indicates a second derivative, which in this case is the acceleration of the chest due to respiration. The chest acceleration multiplied by a constant K indicates both force acting, and work done, on the chest area. Work done in lifting a mass against gravity is the product of the mass, the standard gravitational constant g, and the lifting height, which in this case is the chest displacement. The force acting on the patient's chest is proportional to the mass portion of the patient's body mass residing at the chest area. This mass portion is equal to the patient's body mass index (BMI). The constant K in Eq. 19 can be expressed as g multiplied by the patient's body mass index (BMI), which is the ratio between the patient's body mass in kilograms, and the patient's height in metres.

Transforming the s-domain relationship in Eq. 19 to the time domain and making the substitutions above yields a continuous-time differential equation summarising the pulmonary ventilation model 1100 relating intrapulmonary pressure to chest displacement:

$$\frac{d}{dt}p_A(t) = -gBMI\left(\frac{d^2}{dt^2}d(t) - \frac{RR}{60}d(t)\right) \quad \text{(Eq. 22)}$$

For a discrete-time implementation of the pulmonary ventilation model 1100, the Laplace transform (s-domain) relationship in Eq. 19 may be converted to an equivalent discrete-time model in the Z-transform domain. The conversion of s-domain relationships to Z-domain uses the equivalence $z=e^{sT_s}$ where $T_s$ is the sampling time (the reciprocal of the sampling rate $f_s$). The resulting Z-transform model may be written as:

$$\frac{P_A(z)}{D(Z)} = -gBMI\left(\frac{1 - k_z z^{-1} + z^{-2}}{1 - z^{-1}}\right) \quad \text{(Eq. 23)}$$

where $k_z = 2\cos h(T_s\sqrt{k_1})$ (the hyperbolic cosine).

Transforming Eq. 23 to the discrete-time domain gives the discrete-time derivative of the intrapulmonary pressure:

$$\Delta p_A[n] = -gBMI f_s^2[d[n] - k_z[n]d[n-1] + d[n-2]] \quad \text{(Eq. 24)}$$

where $$k_z[n] = 2\cos h\left(T_s\sqrt{\frac{RR[n]}{60}}\right) \quad \text{(Eq. 25)}$$

to allow for the variation in the respiratory rate RR over time.

Discrete-time integration of Eq. 26 between sampling instants (n−1) and n using the trapezoidal rule yields a third-order difference equation for the instantaneous intrapulmonary pressure $p_A[n]$:

$$p_A[n]=p_A[n-1]-gBMIf_s[d[n]-(k_z[n]-1)d[n-1]+(1-k_z[n-1])d[n-2]+d[n-3]] \quad \text{(Eq. 26)}$$

The intrapulmonary pressure $p_A[n]$ may be converted to an instantaneous lung volume $V_L[n]$ (in millilitres) using Boyle's Law, which states that pressure and volume are inversely proportional:

$$V_L[n] = \begin{cases} V_{TLC}\left[\frac{p_A[n-1]}{p_A[n]} - 1\right], & p_A[n] \neq 0 \\ 0, & p_A[n] = 0 \end{cases} \quad \text{(Eq. 27)}$$

$V_{TLC}$ is the total lung capacity (TLC) in millilitres. Adopting the power law prediction parameters for respiratory variables in mammals by Stahl [2] and the height-weight covariance by Livingston and Lee [3], $V_{TLC}$ can be expressed in the form of an allometric formula, where Wt is the patient's predicted ideal body mass in kilograms and Ht is the patient's actual height in centimeters:

$$V_{TLC} = 53.5 \; Wt^{1.06} \text{ where } Wt = \left(\frac{Ht}{33.34}\right)^{0.3922^{-1}} \quad \text{(Eq. 28)}$$

The range of lung volume $V_L[n]$ over a breath determines the tidal volume Vt for the breath.

FIG. 12 is a flow chart illustrating a method 1200 that may be used to implement an analysis process. The method 1200, such as when implemented as a function of a processor, estimates the cardio-respiratory parameter known as the mean tidal volume Vt from two inputs, the chest displacement signal d[n] and the respiratory rate RR[n]. Like the method 8000, the method 1200 may be carried out by the processor 7006 of the unobtrusive monitoring apparatus 7000 or a processor of the external computing device 7005 in communication therewith. In some such implementations, the chest displacement signal d[n] may be obtained by integrating, using Eq. 18, the chest velocity v[n] obtained from the relative demodulation step 8010 of the method 8000. In such an implementation, the respiratory rate RR[n] may be obtained from the step 8040 of the method 8000.

In other implementations, the chest displacement signal d[n] may be obtained directly, e.g. from a respiratory inductance plethysmogram (respiratory effort sensor) 2040 on a PSG chest band, and the respiratory rate RR[n] may be obtained by conventional analysis of one or more of the other PSG signals.

The method 1200 starts at step 1210, which applies Eq. 26 to estimate the intrapulmonary pressure $p_A[n]$ from the chest displacement signal d[n] and the respiratory rate RR[n]. Step 1220 then applies Eq. 27 to estimate the instantaneous lung volume $V_L[n]$ from the estimated intrapulmonary pressure $p_A[n]$. To reject noise and/or gross bodily movements corrupting the chest displacement signal d[n], the instantaneous lung volume estimate $V_L[n]$ may in some implementations of step 1220 be "clipped" so that its absolute value does not exceed the patient's predicted peak tidal volume $V_{PT}$. According to Stahl [2] and Livingston and Lee [3], $V_{PT}$ can be expressed in the form of an allometric formula using the patient's predicted ideal body mass Wt as described above:

$$V_{PT}=7.69 Wt^{1.04} \quad \text{(Eq. 29)}$$

Step 1230 then applies a respiratory band-pass filter (RBPF), e.g. the RBPF described above in relation to step 8020, to extract the respiratory component of the estimated instantaneous lung volume $V_L[n]$.

The next step 1240 identifies the maximum and minimum values of the respiratory component of the estimated instantaneous lung volume V[n] for each breath. A breath is delineated by the current and previous identified maximum values of the respiratory component of $V_L[n]$. The breath-wise tidal volume Vt is then estimated as the difference between the maximum and the minimum values of the respiratory component of the instantaneous lung volume $V_L[n]$ over each breath. A threshold value of $V_{PT}$ may be applied as a conditional rule, i.e., if the estimated tidal volume Vt for the current breath is greater than the threshold, then the estimated tidal volume Vt for the current breath is set equal to the estimated tidal volume Vt for the previous breath. Step 1250 then calculates the mean of the breathwise tidal volume Vt per selected window. In one implementation, a fixed window-width of 60 seconds (2 epochs) and a sliding window-width of 30 seconds (1 epoch) may be employed.

7.8.3.3.1 Example Results

The mean tidal volume was estimated using the method 1200 applied to the chest displacement obtained using relative demodulation (step 8010) of the example I and Q channel data mentioned above. For comparison, the mean tidal volume was also estimated by applying the steps 1220 to 1250 of the method 1200 to the nasal pressure signal of the parallel PSG data. Across all twenty patients' monitoring sessions, the mean tidal volume estimation achieved 83.1% median accuracy compared to the PSG with median error of 57.3 mL.

7.9 GLOSSARY

For the purposes of the present technology disclosure, in certain forms of the present technology, one or more of the following definitions may apply. In other forms of the present technology, alternative definitions may apply.

7.9.1 General

Air: In certain forms of the present technology, air may be taken to mean atmospheric air, and in other forms of the present technology air may be taken to mean some other combination of breathable gases, e.g. atmospheric air enriched with oxygen.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of expired gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Patient: A person, whether or not they are suffering from a respiratory condition.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

7.9.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inspiratory time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory airflow rate, as opposed to "true respiratory flow rate" or "true respiratory airflow rate", which is the actual respiratory flow rate experienced by the patient, usually expressed in litres per minute.

Tidal volume (Vt): The volume of air inspired or expired during normal breathing, when extra effort is not applied.

Inspiratory Time (Ti): The duration of the inspiratory portion of the respiratory flow rate waveform.

Expiratory Time (Te): The duration of the expiratory portion of the respiratory flow rate waveform.

Total Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

7.10 OTHER REMARKS

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

7.11 REFERENCE SIGNS LIST patient 1000
pulmonary ventilation model 1100
method 1200
step 1210
step 1220
step 1230
step 1240
step 1250
headbox 2000
ground electrode 2010
EOG electrode 2015
EEG electrode 2020
ECG electrode 2025
submental EMG electrode 2030
snore sensor 2035
respiratory effort sensor 2040
respiratory effort sensor 2045
oro-nasal cannula 2050 photoplethysmograph pulse oximeter 2055
body position sensor 2060
patient interface 3000
seal-forming structure 3100
plenum chamber 3200
structure 3300
vent 3400
connection port 3600
forehead support 3700
RPT device 4000
external housing 4010
upper portion 4012
portion 4014
panel 4015
chassis 4016
handle 4018
pneumatic block 4020
inlet air filter 4112
inlet muffler 4122
outlet muffler 4124
pressure generator 4140
blower 4142
air circuit 4170
electrical components 4200
Printed Circuit Board Assembly 4202
electrical power supply 4210
input devices 4220
central controller 4230
therapy device controller 4240
protection circuits 4250
memory 4260
transducers 4270
pressure sensors 4272
flow rate sensors 4274
data communication interface 4280
output devices 4290
humidifier 5000
humidifier inlet 5002
humidifier outlet 5004
humidifier base 5006
humidifier reservoir 5110
humidifier reservoir dock 5130
heating element 5240
monitoring apparatus 7000
microcontroller unit 7001
memory 7002
baseband signal 7003
communications circuitry 7004
external computing device 7005
processor 7006
sensor unit 7007
connection 7008
motion sensor 7010
display device 7015
audio output 7017
transmitter 7020
receiver 7030
local oscillator 7040
single antenna 7050
signals 7060
signal 7070
mixer 7080
method 8000
step 8010
step 8020
step 8030
step 8040
step 8050
step 8060
step 8070
graph 9000
trace 9010
trace 9020

8 CITATIONS

8.1 Patent Literature

8.2 Non-Patent Literature

1. Pan, J. and Tompkins, W. J., *A Real-Time QRS Detection Algorithm.* IEEE Transactions on Biomedical Engineering, 1985. BME-32(3): p. 230-236.
2. W. R. Stahl, *Scaling of respiratory variables in mammals,* Journal of Applied Physiology, vol. 22, no. 3, pp. 453-460, 1967.
3. E. H. Livingston, and S. Lee, *Body surface area prediction in normal-weight and obese patients,* American Journal of Physiology—Endocrinology and Metabolism, vol. 281, no. 3, pp. E586-E591, 2001.

The invention claimed is:

1. A method of estimating a heart rate of a patient from an in-phase channel and a quadrature channel, each channel representing chest movement of the patient, the method comprising:
   in one or more processors,
   processing the in-phase channel and the quadrature channel by relative demodulation to generate a jerk signal, wherein the relative demodulation comprises numerically differentiating the in-phase channel and the quadrature channel to produce a numeric derivative of the in-phase channel and a numeric derivative of the quadrature channel, and generating a chest velocity signal from the numeric derivative of the in-phase channel and the numeric derivative of the quadrature channel;
   filtering the jerk signal with a cardiac band-pass filter to produce a cardiac jerk signal; and
   generating a heart rate estimate from zero-crossings of the cardiac jerk signal.

2. A method according to claim 1, wherein the generating the heart rate estimate comprises:
   detecting systole phases of heartbeats by determination of the zero-crossings of the cardiac jerk signal; and
   calculating the heart rate estimate from a number of detected systole phases in a window of the cardiac jerk signal.

3. A method according to claim 1, wherein the generating the heart rate estimate comprises:
   detecting diastole phases of heartbeats by determination of the zero-crossings of the cardiac jerk signal; and
   calculating the heart rate estimate from a number of detected diastole phases in a window of the cardiac jerk signal.

4. A method according to claim 1, wherein the jerk signal is a third derivative of chest displacement of the patient.

5. A method according to claim 1, wherein the relative demodulation further comprises:
   numerically differentiating the chest velocity signal to generate the jerk signal.

6. A method according to claim 1, wherein the generating the chest velocity signal comprises:
   dividing the numeric derivative of the quadrature channel by the in-phase channel to obtain a first ratio signal;

dividing the numeric derivative of the in-phase channel by the quadrature channel to obtain a second ratio signal; and subtracting the second ratio signal from the first ratio signal multiplied by a scaling factor.

7. A method according to claim 6, wherein the scaling factor is a ratio of amplitude gain constants of the in-phase channel and the quadrature channel.

8. A method according to claim 6, further comprising subtracting respective offsets from the in-phase channel and the quadrature channel before the dividing steps.

9. A method according to claim 1, wherein the cardiac band-pass filter comprises a band-pass filter with a pass-band of 0.7 to 1.6 Hz.

10. A method according to claim 9, wherein the band-pass filter is a sixth-order Butterworth filter.

11. A method according to claim 1, wherein the in-phase channel and the quadrature channel are generated by a contactless motion sensor.

12. A method according to claim 11, wherein the contactless motion sensor is a radio-frequency sensor that generates the in-phase channel and the quadrature channel by processing of signals representing transmitted radio-frequency waves and received reflected ones of the transmitted radio-frequency waves.

13. A method according to claim 1, wherein the one or more processors controls a display to output the heart rate estimate.

14. A method according to claim 1, wherein the one or more processors controls a change to a control parameter of a treatment device in response to the heart rate estimate.

15. A method according to claim 1, wherein the jerk signal is a second derivative of the chest velocity signal.

16. A method according to claim 15, wherein the jerk signal describes changes in acceleration.

17. Apparatus for estimating heart rate of a patient, the apparatus comprising:
a contactless motion sensor configured to generate an in-phase channel and a quadrature channel, wherein the in-phase channel and the quadrature channel each represent chest movement of the patient when the contactless motion sensor is generally directed toward a chest of the patient; and
a processor configured to analyse the in-phase channel and the quadrature channel to generate a heart rate estimate, the analysis comprising:
processing the in-phase channel and the quadrature channel by relative demodulation to generate a jerk signal, wherein the relative demodulation comprises numerically differentiating the in-phase channel and the quadrature channel to produce a numeric derivative of the in-phase channel and a numeric derivative of the quadrature channel, and generating a chest velocity signal from the numeric derivative of the in-phase channel and the numeric derivative of the quadrature channel;
filtering the jerk signal with a cardiac band-pass filter to produce a cardiac jerk signal; and
generating a heart rate estimate from zero-crossings of the cardiac jerk signal.

18. Apparatus according to claim 17, wherein the processor is co-located with the contactless motion sensor.

19. Apparatus according to claim 17, further comprising communications circuitry configured to transfer data to an external computing device via a connection.

20. Apparatus according to claim 19, wherein the processor is a processor of the external computing device.

21. Apparatus according to claim 17, wherein the contactless motion sensor is a radio-frequency sensor that generates the in-phase channel and the quadrature channel by processing of signals representing transmitted radio-frequency waves and received reflected ones of the transmitted radio-frequency waves.

22. Apparatus according to claim 17, wherein the jerk signal is a second derivative of the chest velocity signal.

23. Apparatus according to claim 22, wherein the jerk signal describes changes in acceleration.

24. A method of estimating a respiratory rate of a patient from an in-phase channel and a quadrature channel, each channel representing chest movement of the patient, the method comprising:
in one or more processors,
processing the in-phase channel and the quadrature channel by relative demodulation to generate a chest velocity signal, wherein the relative demodulation comprises numerically differentiating the in-phase channel and the quadrature channel to produce a numeric derivative of the in-phase channel and a numeric derivative of the quadrature channel, and generating the chest velocity signal from the numeric derivative of the in-phase channel and the numeric derivative of the quadrature channel;
filtering the chest velocity signal with a respiratory band-pass filter to produce a respiratory velocity signal; and
generating a respiratory rate estimate from zero-crossings of the respiratory velocity signal.

25. A method according to claim 24, wherein the generating the respiratory rate estimate comprises:
detecting inspiration phases of respiration by determination of the zero-crossings of the respiratory velocity signal; and
calculating the respiratory rate estimate from a number of detected inspiration phases in a window of the respiratory velocity signal.

26. A method according to claim 24, wherein the generating the respiratory rate estimate comprises:
detecting expiration phases of respiration by determination of the zero-crossings of the respiratory velocity signal; and
calculating the respiratory rate estimate from a number of detected expiration phases in a window of the respiratory velocity signal.

27. A method according to claim 24, wherein the chest velocity signal is a first derivative of chest displacement of the patient.

28. A method according to claim 24, wherein the generating the chest velocity signal comprises:
dividing the numeric derivative of the quadrature channel by the in-phase channel to obtain a first ratio signal;
dividing the numeric derivative of the in-phase channel by the quadrature channel to obtain a second ratio signal; and
subtracting the second ratio signal from the first ratio signal multiplied by a scaling factor.

29. A method according to claim 28, wherein the scaling factor is a ratio of amplitude gain constants of the in-phase channel and the quadrature channel.

30. A method according to claim 28, further comprising subtracting respective offsets from the in-phase channel and the quadrature channel before the dividing steps.

31. A method according to claim 24, wherein the respiratory band-pass filter comprises a band-pass filter with a pass-band of 0.2 to 0.5 Hz.

32. A method according to claim 31, wherein the band-pass filter is a sixth-order Butterworth filter.

33. A method according to claim 24, wherein the in-phase channel and the quadrature channel are generated by a contactless motion sensor.

34. A method according to claim 33, wherein the contactless motion sensor is a radio-frequency sensor that generates the in-phase channel and quadrature channel by processing of signals representing transmitted radio-frequency waves and received reflected ones of the transmitted radio-frequency waves.

35. A method according to claim 24, wherein the one or more processors controls a display to output the respiratory rate estimate.

36. A method according to claim 24, wherein the one or more processors controls a change to a control parameter of a treatment device in response to the respiratory rate estimate.

37. Apparatus for estimating respiratory rate of a patient, the apparatus comprising:
 a contactless motion sensor configured to generate an in-phase channel and a quadrature channel, each channel representing chest movement of the patient when the contactless motion sensor is generally directed toward a chest of the patient; and
 a processor configured to analyse the in-phase channel and the quadrature channel to generate a respiratory rate estimate, the analysis comprising:
 processing the in-phase channel and the quadrature channel by relative demodulation to generate a chest velocity signal, wherein the relative demodulation comprises numerically differentiating the in-phase channel and the quadrature channel to produce a numeric derivative of the in-phase channel and a numeric derivative of the quadrature channel, and generating the chest velocity signal from the numeric derivative of the in-phase channel and the numeric derivative of the quadrature channel;
 filtering the chest velocity signal with a respiratory band-pass filter to produce a respiratory velocity signal; and
 generating a respiratory rate estimate from zero-crossings of the respiratory velocity signal.

38. Apparatus according to claim 37, wherein the processor is co-located with the contactless motion sensor.

39. Apparatus according to claim 37, further comprising communications circuitry configured to transfer data to an external computing device via a connection.

40. Apparatus according to claim 39, wherein the processor is a processor of the external computing device.

41. Apparatus according to claim 37, wherein the contactless motion sensor is a radio-frequency sensor that generates the in-phase channel and the quadrature channel by processing of signals representing transmitted radio-frequency waves and received reflected ones of the transmitted radio-frequency waves.

42. A patient monitoring system comprising:
 means for generating an in-phase channel and a quadrature channel, each channel representing chest movement of a patient; and
 means for analysing the in-phase channel and the quadrature channel to generate a heart rate estimate of the patient, the analysing comprising:
 processing the in-phase channel and the quadrature channel by relative demodulation to generate a jerk signal, wherein the relative demodulation comprises numerically differentiating the in-phase channel and the quadrature channel to produce a numeric derivative of the in-phase channel and a numeric derivative of the quadrature channel, and generating a chest velocity signal from the numeric derivative of the in-phase channel and the numeric derivative of the quadrature channel;
 filtering the jerk signal with a cardiac band-pass filter to produce a cardiac jerk signal; and
 generating a heart rate estimate from zero-crossings of the cardiac jerk signal.

43. A patient monitoring system comprising:
 means for generating an in-phase channel and a quadrature channel, each channel representing chest movement of a patient; and
 means for analysing the in-phase channel and the quadrature channel to generate a respiratory rate estimate of the patient, the analysing comprising:
 processing the in-phase channel and the quadrature channel by relative demodulation to generate a chest velocity signal, wherein the relative demodulation comprises numerically differentiating the in-phase channel and the quadrature channel to produce a numeric derivative of the in-phase channel and a numeric derivative of the quadrature channel, and generating the chest velocity signal from the numeric derivative of the in-phase channel and the numeric derivative of the quadrature channel;
 filtering the chest velocity signal with a respiratory band-pass filter to produce a respiratory velocity signal; and
 generating a respiratory rate estimate from zero-crossings of the respiratory velocity signal.

\* \* \* \* \*